US011540912B1

(12) United States Patent
Bernshtein

(10) Patent No.: US 11,540,912 B1
(45) Date of Patent: Jan. 3, 2023

(54) BRANCH STENT FOR IMPLANTATION FROM A MAIN BLOOD VESSEL AND DEPLOYMENT METHODS

(71) Applicant: Bifsol Technologies LTD., Haifa (IL)

(72) Inventor: Vadim Bernshtein, Haifa (IL)

( * ) Notice: Subject to any disclaimer, the term of this patent is extended or adjusted under 35 U.S.C. 154(b) by 0 days.

(21) Appl. No.: 17/659,212

(22) Filed: Apr. 14, 2022

(51) Int. Cl.
*A61F 2/07* (2013.01)
*A61F 2/954* (2013.01)
*A61F 2/06* (2013.01)

(52) U.S. Cl.
CPC .............. *A61F 2/07* (2013.01); *A61F 2/954* (2013.01); *A61F 2002/061* (2013.01); *A61F 2002/065* (2013.01); *A61F 2250/0039* (2013.01)

(58) Field of Classification Search
CPC ...... A61F 2/07–2002/077; A61F 2/954; A61F 2250/006; A61F 2250/0069–007; A61F 2002/821
See application file for complete search history.

(56) References Cited

U.S. PATENT DOCUMENTS

| | | | | |
|---|---|---|---|---|
| 2005/0154444 | A1* | 7/2005 | Quadri | A61F 2/07 623/1.13 |
| 2007/0043420 | A1* | 2/2007 | Lostetter | A61F 2/95 623/1.11 |
| 2007/0055360 | A1* | 3/2007 | Hanson | A61F 2/07 623/1.35 |
| 2008/0167704 | A1* | 7/2008 | Wright | A61F 2/954 623/1.23 |
| 2009/0099648 | A1* | 4/2009 | Yu | A61F 2/954 623/1.13 |

(Continued)

FOREIGN PATENT DOCUMENTS

GB  2515731 A  * 1/2015 ............... A61F 2/07

OTHER PUBLICATIONS

K Craig Kent, "Clinical practice. Abdominal aortic aneurysms", The New England Journal of Medicine, vol. 371, Issue 22, pp. 2101-2108, Nov. 2014.

(Continued)

*Primary Examiner* — Rebecca S Preston
(74) *Attorney, Agent, or Firm* — Haim M. Factor—1st-Tech-Ideas

(57) ABSTRACT

A branch stent for implantation from a main blood vessel in a plurality of branch blood vessels having respective branch blood vessel diameters, the branch stent comprising: a tubular element having: an axis of elongation; a first and a second tubular element end; the tubular element covered with a tubular element cover; and a parachute element having an unconstrained flat-toroid/disc configuration, the parachute element having a parachute element cover, the parachute element positioned perpendicularly at the second tubular element end, and positioned coaxially to the axis of elongation; wherein the branch stent is implanted from within a fenestrated stent-graft having oversized fenestrations, the fenestrated stent-graft first implanted in the main blood vessel at a bifurcation zone including the plurality of branch blood vessels, with each of the oversized fenestrations having respective diameters larger than respective branch blood vessel diameters; wherein the branch stent and the fenestrated stent-graft are together a multi-stent.

4 Claims, 19 Drawing Sheets

(56) References Cited

U.S. PATENT DOCUMENTS

2016/0184077 A1* 6/2016 Choubey ............... A61F 2/07
623/1.13
2019/0388213 A1* 12/2019 Torrance ............. A61F 2/958

OTHER PUBLICATIONS

Tang et al., "Lifetime Risk and Risk Factors for Abdominal Aortic Aneurysm in a 24-Year Prospective Study the ARIC Study (Atherosclerosis Risk in Communities)", Arterioscler Thromb Vasc Biol, pp. 2468-2477, Dec. 2016.

Veronika Kessler et al., "AAA Revisited: A Comprehensive Review of Risk Factors, Management, and Hallmarks of Pathogenesis", Biomedicines, 10, 94, pp. 1-35, Jan. 2, 2022.

Carpenter et al., "Impact of exclusion criteria on patient selection for endovascular abdominal aortic aneurysm repair", Journal of Vascular Surgery, vol. 34, No. 6, pp. 1050-1054, Dec. 2001.

Abbruzzese et al., "Outcomes following endovascular abdominal aortic aneurysm repair (EVAR): An anatomic and device-specific analysis", Journal of Vascular Surgery, pp. 19-28, Jul. 2008.

I. Banzic et al., "Morphological Differences in the Aorto-iliac Segment in AAA Patients of Caucasian and Asian Origin", European Journal of Vascular and Endovascular Surgery, vol. 51, Issue 6, pp. 783-789, Jun. 2016.

Lo et al., "Gender differences in abdominal aortic aneurysm presentation, repair, and mortality in the Vascular Study Group of New England", Journal of Vascular Surgery, vol. 57, issue 5, pp. 1261-1268, May 2013.

Scali at el., "Critical analysis of results after chimney endovascular aortic aneurysm repair raises cause for concern", Journal of Vascular Surgery, vol. 60, Issue 4, pp. 865-874, Oct. 2014.

Lee et al., "Early experience with the snorkel technique for juxtarenal aneurysms", Journal of Vascular Surgery, vol. 55, Issue 4, pp. 935-946, Apr. 2012.

Moulakakis et al., "The chimney-graft technique for preserving supra-aortic branches: a review", Annals of Cardiothoracic Surgery, vol. 2, Issue 3, pp. 339-346, May 2013.

W. Guo, T. Zhang, "Abdominal Aortic Aneurysm Prevalence in China", Endovascular Today, pp. 76-82, Feb. 2014.

B. Colvard, J. T. Le, "Early Detection of Type 1 Endoleaks", Endovascular Today, pp. 41-44, Feb. 2013.

Schepens et al., "Indications for Thoracoabdominal Aortic Surgery", The Journal of Thoracic and Cardiovascular Surgery, vol. 140, pp. S121-S124, Dec. 2010.

Verzini et al., "A Preliminary Analysis of Late Structural Failures of the Navion Stent Graft in the Treatment of Descending Thoracic Aortic Aneurysms", Journal of Vascular Surgery, Article in Press—Apr. 19, 2021.

Shanzer et al., "Predictors of Abdominal Aortic Aneurysm Sac Enlargement After Endovascular Repair", Circulation, 123(24), pp. 2848-2855, Jun. 2011.

G. A. Antoniou at el., "A meta-analysis of outcomes of endovascular abdominal aortic aneurysm repair in patients with hostile and friendly neck anatomy", Journal of Vascular Surgery, vol. 57, Issue 2, pp. 527-538, Feb. 2013.

Cristiana Catenaa, GianLuca Colussia, Gabriele Brosoloa, Nicolas Verheyenb, Marileda Novelloa, Nicole Bertina, Messandro Cavarapea, Leonardo A. Sechi; Long-Term Renal and Cardiac Outcomes after Stenting in Patients with Resistant Hypertension and Atherosclerotic Renal Artery Stenosis, Kidney Blood Press Res 2017; vol. 42:pp. 774-783.

Chrysochou C, Kalra PA. Epidemiology and natural history of athero-sclerotic renovascular disease. Prog Cardiovasc Dis 2009; 52(3): 184-195. doi:10.1016/j.pcad.2009.09.001.

Mina M. Benjamin, Poorya Fazel, Giovanni Filardo, James W. Choi and Robert C. Stoler, Prevalence of and Risk Factors of Renal Artery Stenosis in Patients With Resistant Hypertension, Systemic Hypertension| vol. 113, Issue 4, p. 687-690, Feb. 15, 2014.

Thom W. Rooke, Alan T. Hirsch et al; Management of patients with peripheral artery disease (compilation of 2005 and 2011 ACCF/AHA Guideline Recommendations. Journal of the American College of Cardiology, vol. 61, No. 14, 2013, http://dx.doi.org/10.1016/j.jacc.2013.01.004.

Andreas Grüntzig, Wilhelm Vetter, Bernhard Meier, Ulrich Kuhlmann, Urs Lütolf, Walter Siegenthaler, Treatment of Renovascular Hypertension With Percutaneous Transluminal Dilatation of a Renal-Artery Stenosis, Lancet, vol. 311, Issue 8068, p. 801-802, Apr. 15, 1978.

Steven R. Bailey, Joshua A. Beckman and Timothy D. Dao, ACC/AHA/SCAI/SIR/SVM 2018 appropriate use criteria for peripheral artery intervention: a report of the American College of Cardiology Appropriate Use Criteria Task Force, American Heart Association, Society for Cardiovascular Angiography and Interventions, Society of Interventional Radiology, and Society for Vascular Medicine. Journal of the American College of Cardiology, vol. 73, No. 2, 2019, pp. 214-237.

Sahil A. Parikh , Mehdi H. Shishehbor, Bruce H. Gray, Christopher J. White, and Michael R. Jaff, SCAI expert consensus statement for renal artery stenting appropriate use. Catheterization & Cardiovascular Interventions 2014, vol. 84(7): pp. 1163-1171.

Christopher J. Cooper, Timothy P. Murphy, Donald E. Cutlip et al. CORAL Investigators.; Stenting and Medical Therapy for Atherosclerotic Renal-Artery Stenosis, The new england journal o f medicine, Jan. 2, 2014 vol. 370 No. 1, pp. 13-22.

ASTRAL Investigators; Wheatley K, Ives N, Gray R, et al. Revascularization versus medical therapy for renal-artery stenosis. The new england journal o f medicine, Nov. 12, 2009; vol. 361(20); pp. 1953-1962.

* cited by examiner

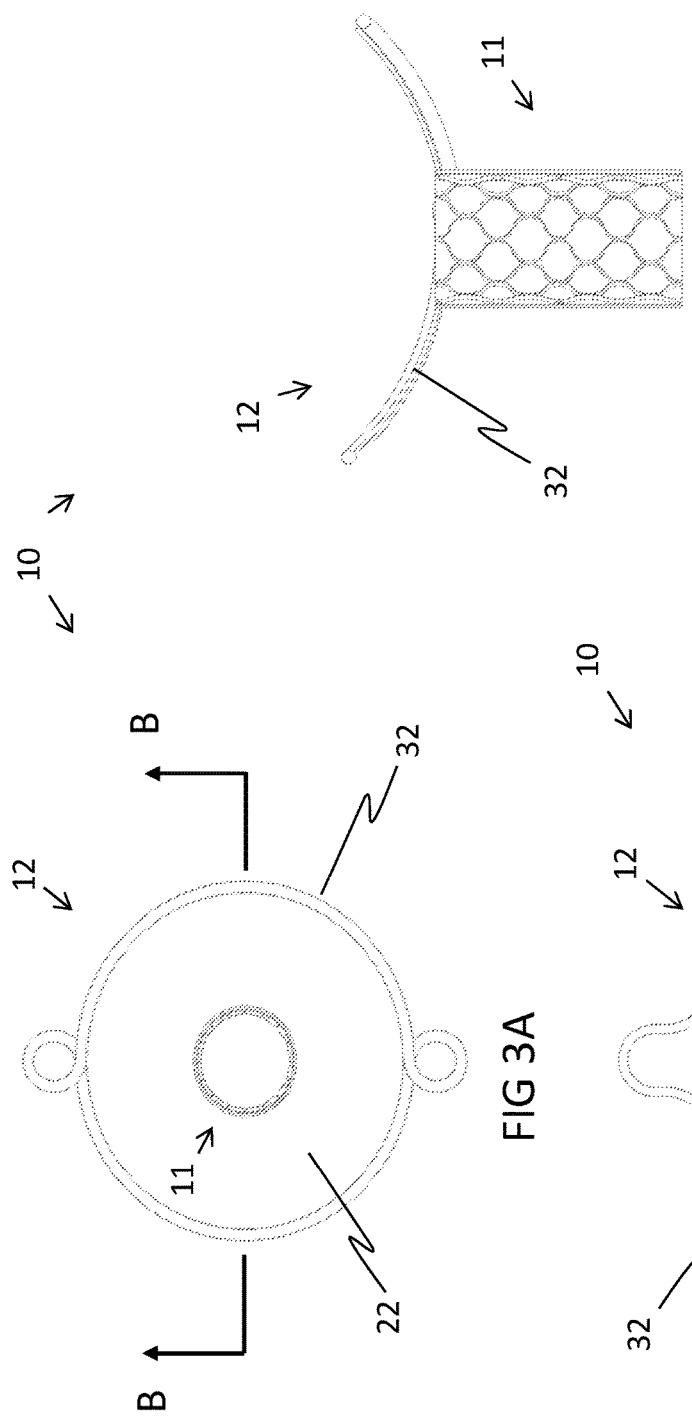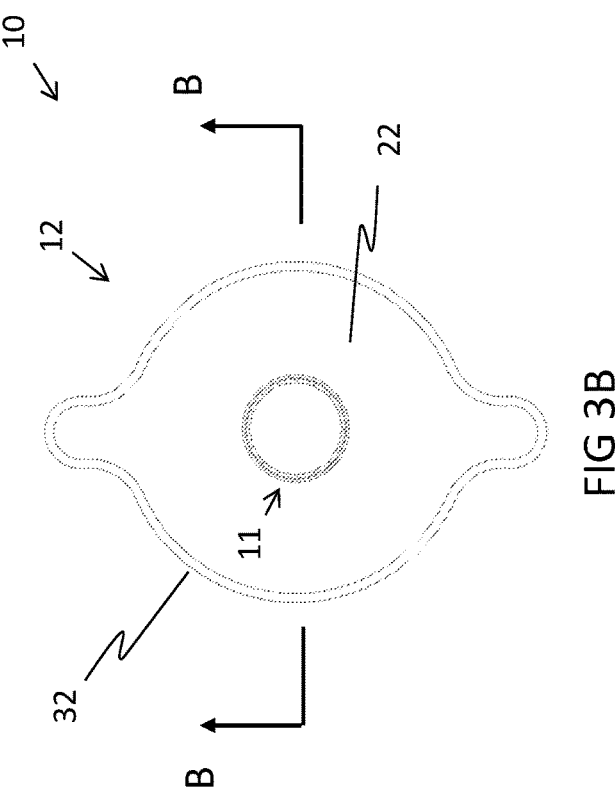

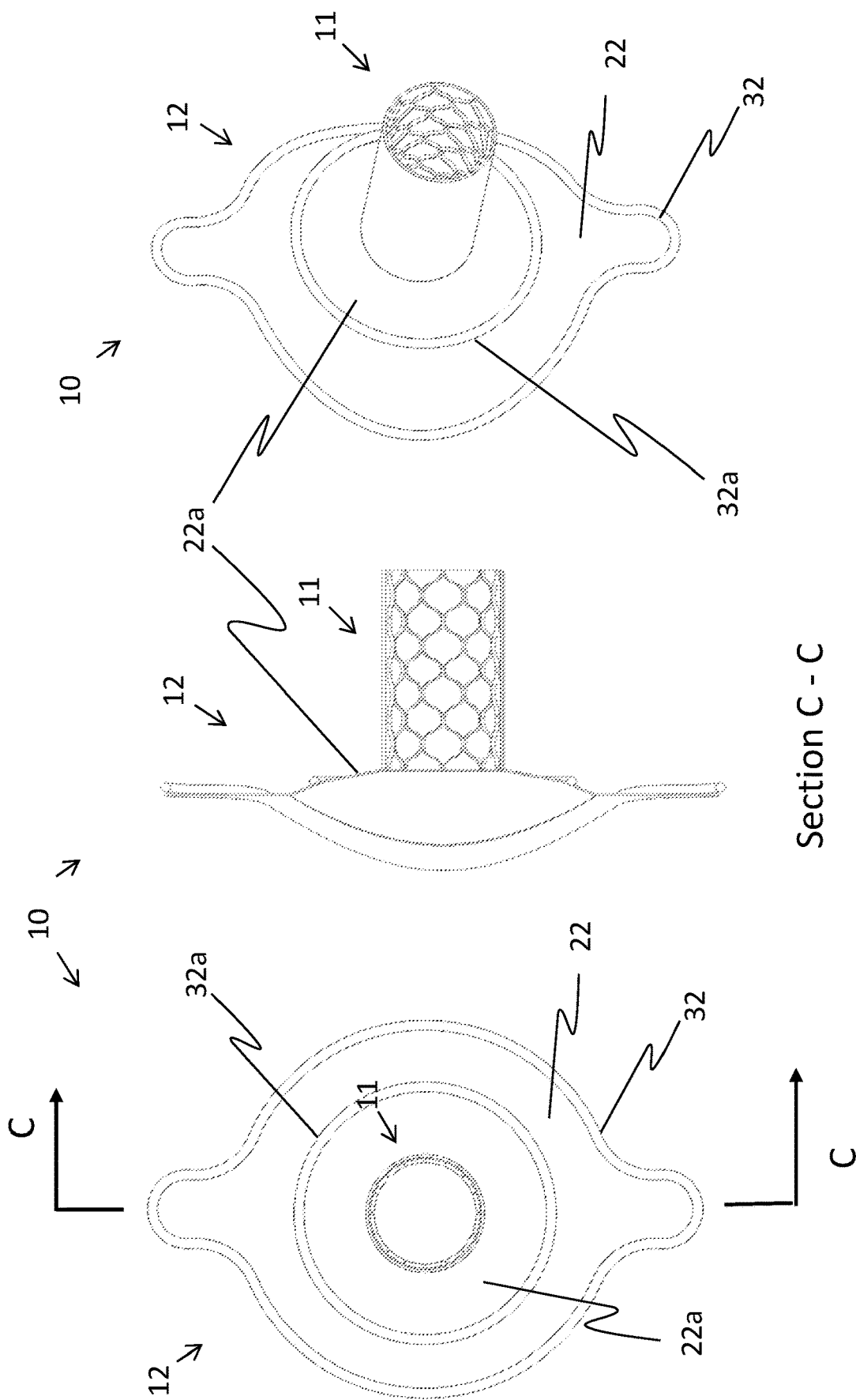

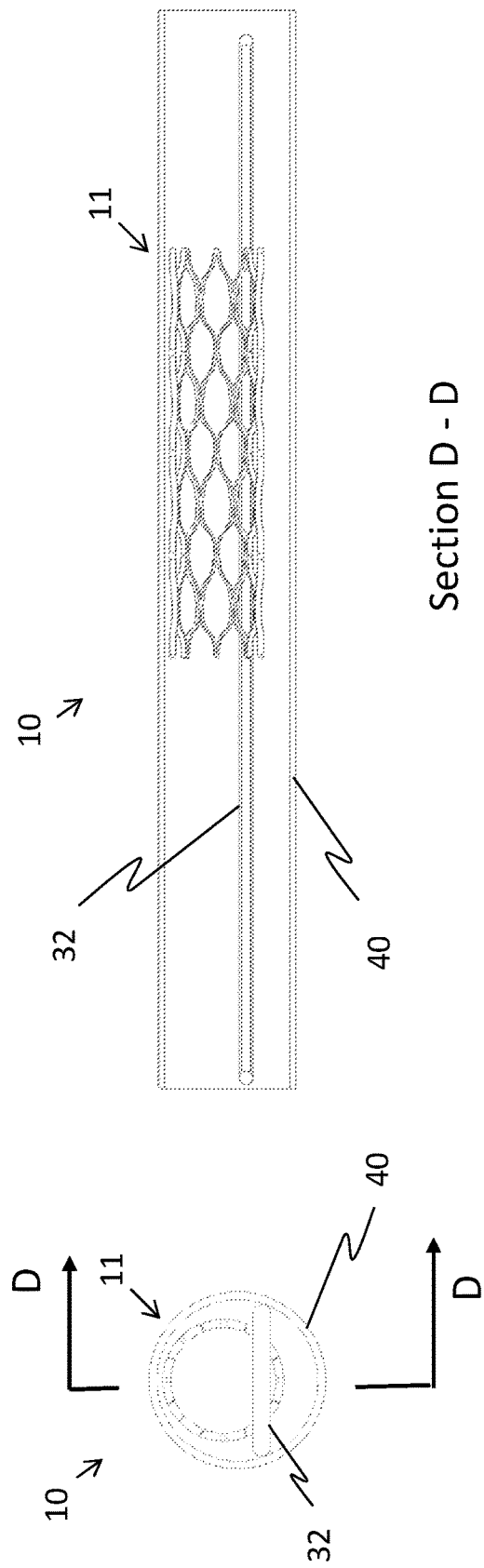

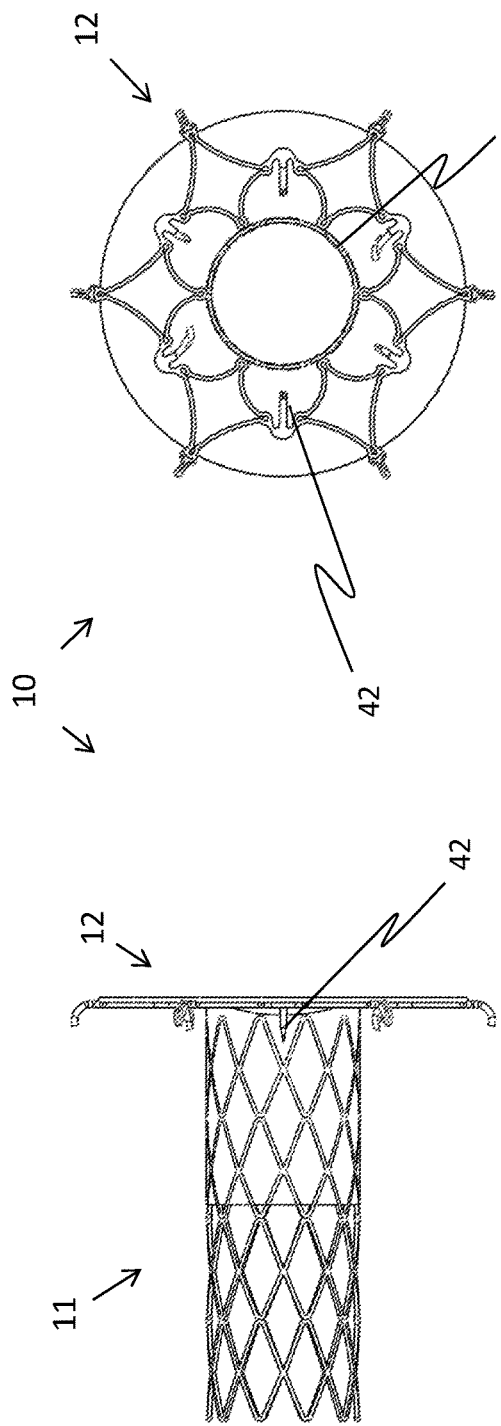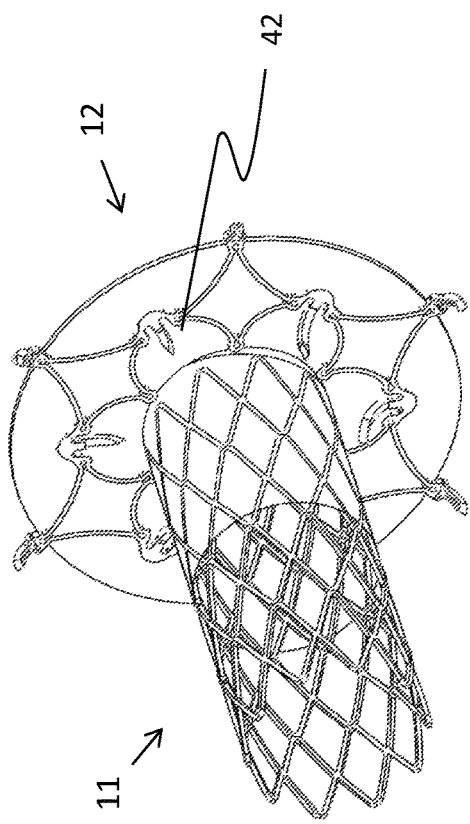

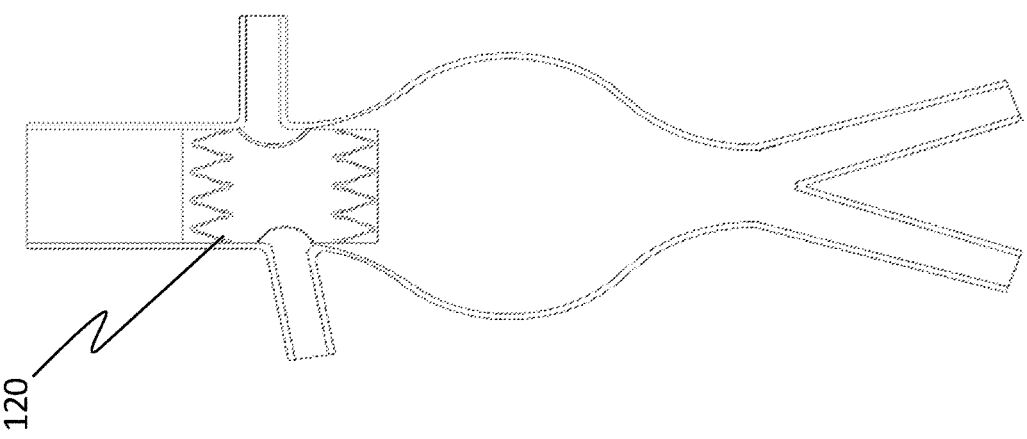

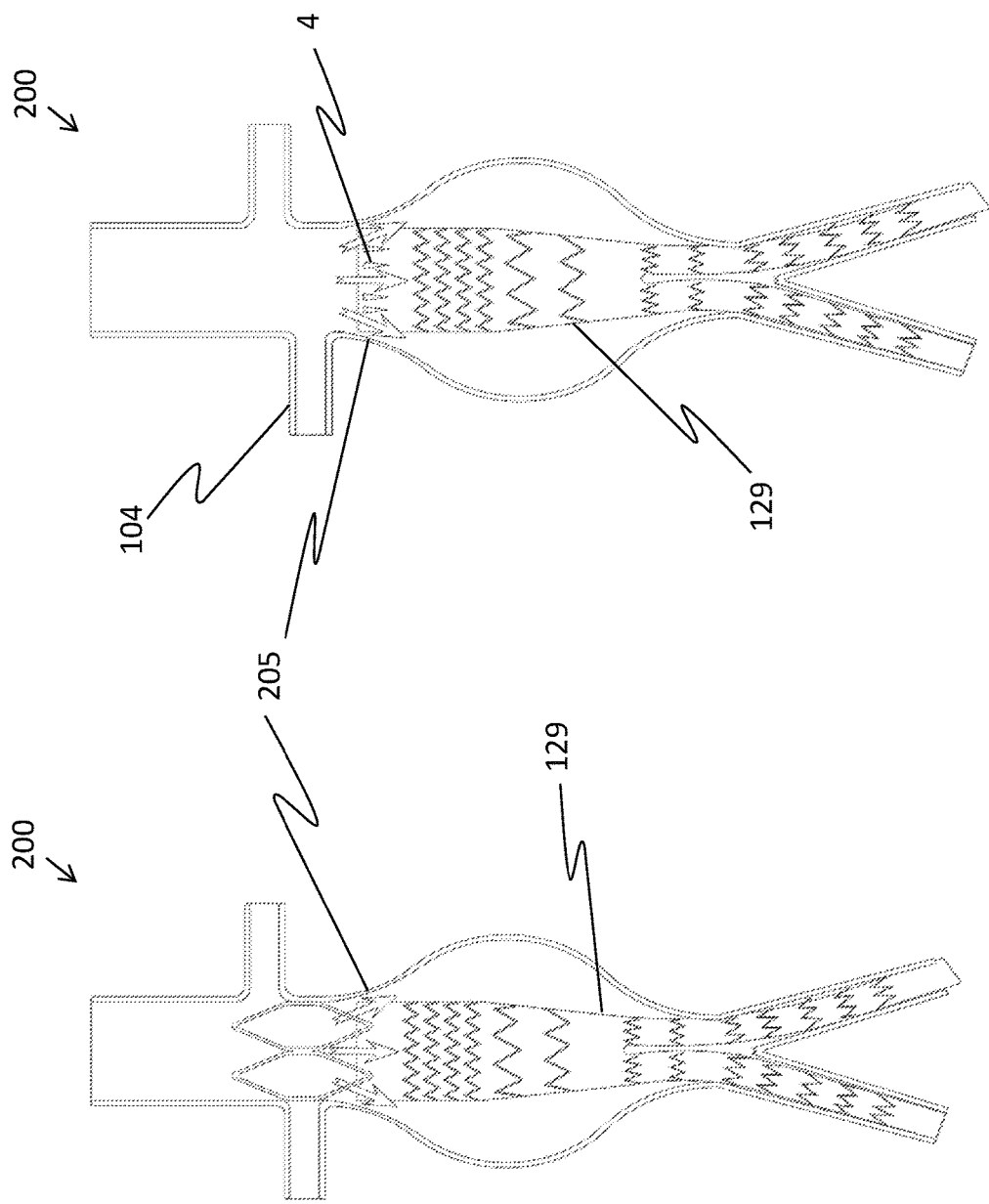

BRANCH STENT FOR IMPLANTATION FROM A MAIN BLOOD VESSEL AND DEPLOYMENT METHODS

FIELD OF THE INVENTION AND BACKGROUND

The current invention relates to medical stents in general, and specifically to low crimp intravascular bifurcation zone implants and deployment methods thereof. In the specification and claims which follow hereinbelow, the term "implant" is a general term, interchangeable with "intravascular device"—both terms herein intended to mean "stent-graft"—as known in the art. The terms "bifurcation zone" and "bifurcation", and variations thereof, as used in the specification and claim which follow hereinbelow, are intended to mean points/places/zones in the vascular system where at least one secondary/side blood vessel branches out of a typically larger, main artery/blood vessel. The terms, "stent" or "branch component" are intended to mean a tubular-shaped implant that connects a stent graft with side-branch blood vessels, thereby allowing natural blood flow to vital organs.

The term "delivery system", as used in the specification and claims which follow hereinbelow, is intended to mean a catheter and associated components, used to deliver and deploy an implant. Part of the catheter is a tube, as known in the art. The term "sheath", as used in the specification and claims which follow hereinbelow, is intended to mean a containment configuration/enclosure of one or more crimped stents. The sheath is included in the tube of the delivery system, as known in the art. Additional components of the delivery system include, but are not limited to guidewires and other wire/activation mechanisms, typically included within the catheter. The catheter is characterized by a "distal end", meaning the end of the catheter inserted into the body towards/at the bifurcation zone, and a "proximal end", meaning the end of the catheter extending out of the body, from where the delivery system is activated/manipulated by a skilled individual—all as known in the art. Typically, the sheath is located substantially at or near the distal end of the catheter.

The term "chronology", as used in the specification and claims which follow hereinbelow, when used to describe an implant procedure, is intended to mean the overall time and/or sequence of sub-procedures involved in an implant procedure or operation. The duration and number of sub-procedures and/or their complexity contribute to a longer chronology. Therefore, the term "chronology" is used interchangeably herein below to additionally mean the sequence, relative complexity, and/or to several sub-procedures involved in an implant procedure or operation. It is generally desirable to perform fewer and/or less time-consuming operations in a procedure. It is for this reason that shortening or lowering the chronology in an implant procedure is desirable.

A stent is placed or implanted within a vein, an artery, or another tubular body organ, as known in the art, for treating an occlusion, stenosis, aneurysm, collapse, dissection, or weakened, diseased, or abnormally dilated vessel or vessel wall, inter alia, by expanding the vessel and/or by reinforcing the vessel wall. In particular, stents are quite commonly implanted into locations such as, but not limited to: coronary, cardiac, pulmonary, neurovascular, peripheral vascular, renal, gastrointestinal, and reproductive systems.

Two important prior art applications for stents are directed to improving angioplasty results by preventing elastic recoil and remodeling of the vessel wall and for treating dissections in blood vessel walls caused by balloon angioplasty of coronary and peripheral arteries, by pressing intimal flaps together in a lumen at the site of dissection. Conventional stents have been used with limited success rates for treating more complex vascular problems, such as lesions at or near bifurcation zones.

Conventional stent technology is relatively well-developed. Conventional stent designs typically feature a straight tubular-shape having a single-type cellular structure, configuration, or pattern, which is repetitive along the stent longitudinal axis. In many stent designs, the repeating configuration has the strut and connecting-balloon catheter portions that can serve to impede blood flow at bifurcations. In addition to various implant configurations addressing bifurcation stenting, there are many methods for delivering a stent at or near a bifurcation point, the methods commonly called Fenestrated Endovascular Repair (FEVAR), in addition to endovascular aneurysm repair (EVAR), as known in the art.

The discussion which follows presents prior art, which has identified and/or attempted to address the problem.

Craig Kent, in "Clinical practice. Abdominal aortic aneurysms", The New England Journal of Medicine, Vol. 371, Issue 22, pp. 2101-2108, November 2014, whose disclosure is incorporated by reference, describes an abdominal aortic aneurysm, which is a common disease in Western countries. The author proceeds to cite that the prevalence of AAA is 2.2 to 8% among men 65 to 80 years of age and the rates among women are one-fourth as high.

In the US alone, an estimated 1.5 million people have AAA, and more than 200,000 new diagnoses are made each year—as reported by Tang et al., "Lifetime Risk and Risk Factors for Abdominal Aortic Aneurysm in a 24-Year Prospective Study the ARIC Study (Atherosclerosis Risk in Communities)", Arterioscler Thromb Vasc Biol, pp. 2468-2477, December 2016.

Approximately 150,000-200,000 deaths per year worldwide can be attributed to AAA rupture, as reported by Veronika Kessler et al., "AAA Revisited: A Comprehensive Review of Risk Factors, Management, and Hallmarks of Pathogenesis", Journal of Vascular Surgery, pp. 19-28, July 2008. Biomedicines, 10, 94, pp. 1-35, Jan. 2, 2022.

Reference is currently made to FIG. 1A, which is a schematic view of a typical aortic renal zone 2 having an endovascular aneurysm and a prior art endovascular aneurysm repair (EVAR) implant 3. Prior art implant 3 is characterized by a plurality of fixation or anchoring barbs 4; a main body 5; a contralateral gate 7; a contralateral limb extension 8; and an ipsilateral limb 9, in the treatment of Abdominal Aortic Aneurysms (AAA)—all as known in the art.

Reference is additionally made to FIGS. 1B-1E, which are schematic diagrams of respective morphologies of Infrarenal (1B), Juxtarenal (1C), Pararenal (1D), and Suprarenal (1E) AAA—as known in the art—showing variations (2b, 2c, 2d, 2e) of aortic renal zone 2 of FIG. 1A. An "aortic neck" (also referred to hereinbelow as "neck") is indicated by dimension "a", shown in FIGS. 1B and 1C. In prior art Juxtarenal/Suprarenal AAA repair, the presence of an aortic neck is necessary to receive fixation barbs 4 (ref FIG. 1A), which are used to anchor the implant onto the neck and to prevent a Type I endoleak. As such, the variations (2b, 2c, 2d, 2e) of typical aortic renal zone configuration corresponding, respectively, to Juxtarenal, Pararenal, and Suprarenal AAA's are increasingly difficult/improbable choices for such repairs.

Carpenter et al., "Impact of exclusion criteria on patient selection for endovascular abdominal aortic aneurysm repair", Journal of Vascular Surgery, Vol. 34, Num. 6, pp. 1050-1054, December 2001, whose disclosure is incorporated by reference, note that 34% of potential patients treated by minimally invasive procedure failed by exclusion criteria of the products (54% from failure because of a short neck, 40% because of the wide neck and 14% neck angulation).

A large single-center experience reported that women were more often treated outside EVAR instructions for use criterion due to neck length (7.1% vs 1.3%)—as reported by Abbruzzese et al., "Outcomes following endovascular abdominal aortic aneurysm repair (EVAR): An anatomic and device-specific analysis", Journal of Vascular Surgery, pp. 19-28, July 2008.

Additionally, there are significant morphological differences in aorto-iliac segment in AAA patients of European and Asian origin. In comparison, left common femoral artery and right common femoral artery diameters for Caucasian and Asian patients, may differ by about 63-69% of their diameters—as reported by I. Banzic et al., "Morphological Differences in the Aorto-iliac Segment in AAA Patients of Caucasian and Asian Origin", European Journal of Vascular and Endovascular Surgery, Vol. 51, Issue 6, pp. 783-789, June 2016. A parameter such as an artery diameter is critical and serves to define whether a procedure may be performed or not.

An additional solution for the treatment of AAA is the Chimney (also known as "Snorkel") technique, as known in the art. In this method, the aortic stent graft and one or more of the branch stents are implanted simultaneously in the bifurcation zone, usually using opposing-direction of transcatheter approaches. For example, a stent-graft is implanted through a trans-femoral approach, and side-branch stents are implanted through right subclavian, right carotid, left carotid, and left subclavian arteries. The Chimney technique allows for a quick and cheap solution for urgent aneurysm cases, in place of time-consuming and expensive custom-made FEVAR options.

However, a major reason why physicians continue to use the Chimney technique (also called "ChEVAR") is the lack of other alternatives to supply a quick solution for the extremely mortal disease. The Chimney technique has many disadvantages, such as a high-risk for stroke (3.2-5% stroke related mortality), because of the required manipulation of brachiocephalic vessels. Following the Chimney procedure, 20% of patients experienced kidney injury, as reported by Scali et al., "Critical analysis of results after chimney endovascular aortic aneurysm repair raises cause for concern", Journal of Vascular Surgery, Volume 60, Issue 4, pp. 865-874, October 2014.

Lee et al., "Early experience with the snorkel technique for juxtarenal aneurysms", Journal of Vascular Surgery, Volume 55, Issue 4, pp. 935-946, April 2012., report that ChEVAR has a relatively high 30-day mortality rate of 7.1%, and 3-month mortality rate of 10.7%. Type Ia endoleaks following ChEVAR appear in about 14% of cases, as reported by Moulakakis et al., "The chimney-graft technique for preserving supra-aortic branches: a review", Annals of Cardiothoracic Surgery, Volume 2, Issue 3, pp. 339-346, May 2013.

In the case of one or several component failures, the only solution to fix the problem is to perform an open surgical intervention—which is an unacceptable risk for high-risk patients. ChEVAR is additionally limited for small aorta diameters, typically for women and Asian origin patients' as reflected by W. Guo, T. Zhang, "Abdominal Aortic Aneurysm Prevalence in China", Endovascular Today, pp. 76-82, February 2014.

Blood vessel morphology is also a limitation for EVAR procedures. Even for traditional Infrarenal (1B), morphology, after successful AAA implantation, a post-procedure endoleak may occur. The typical reason for such an event to occur is stent-graft migration or proximal aortic neck dilatation in the zone of the proximal stent graft's ring. As a result, the most critical event is the endoleak type I, due to continued pressurization of the aortic sac, which may lead to late rupture of aneurysms. In this case, they require intervention as soon as they are encountered. The overall incidence of early and late-type I endoleaks is thought to be as much as 20%, depending on the series, device, and local practice patterns, with intraoperative type I endoleaks reported at a rate of 3% to 7%, as reported by B. Colvard, J. T. Le, "Early Detection of Type I Endoleaks", Endovascular Today, pp. 41-44, February 2013.

In addition to AAA, Thoracic aortic aneurysms (TAA) are a life-threatening condition causing significant short and long-term mortality due to rupture and dissection. An aneurysm is defined as a dilatation of the aorta of greater than 150% of its normal diameter for a given segment. For the thoracic aorta, a diameter greater than 3.5 cm is generally considered dilatated, whereas greater than 4.5 cm would be considered aneurysmal. Aneurysms may affect one or more segments of the thoracic aorta, including the ascending aorta, the arch, and the descending thoracic aorta. Bret P Nelson, (October 2015), "Thoracic Aneurysm". Medscape. Retrieved 2017-04-16, reports that as many as 25% of patients with TAA also have an abdominal aortic aneurysm. The aortic arch branch vessels, brachiocephalic, left common carotid, and left subclavian arteries, may be part of the aneurysm or maybe close to it.

Prior art implant procedures have accompanying risks, complexity, and expenses, along with concomitantly long procedural chronologies—as outlined hereinabove. There is a need for implant configurations and associated techniques that can allow effective crimping of stents to address aorta and bifurcation branches, employing a singular procedure and/or minimal sub-procedures, thereby yielding minimal and/or a reduced chronology and having concomitant higher success rates (and/or lower risks) in the short and long run. As presented above, an EVAR solution for pre-and post-operation in the aortic suprarenal and arch zones is needed—including novel crimping and deployment techniques for bifurcation stents and temporary embolic protection devices as part of a complex scaffolding that includes a main vessel device supporting branch components/side stents for passive and active functional use.

Such implants and techniques would be especially beneficial for endovascular Juxtarenal, Pararenal, and Suprarenal Abdominal Aortic Aneurysm (AAA) and analogous Thoracic Aortic Aneurysm (TAA) procedures/repairs.

SUMMARY OF THE INVENTION

According to one aspect of the present invention, there is provided a branch component configured for implantation from a main blood vessel in a plurality of branch blood vessels, the main blood vessel having an aneurysm sac therein, the plurality of branch blood vessels having respective branch blood vessel diameters, the branch component being a branch stent initially crimped when delivered by a delivery system, the branch stent comprising: a tubular element having an unconstrained shape, including: an axis of elongation; a first tubular element end; and a second tubular element end; the tubular element covered with a tubular element cover; and a parachute element having an unconstrained shape, including a substantially flat-toroid/disc configuration, the parachute element having a parachute element cover, the parachute element positioned substantially perpendicularly at the second tubular element end, and positioned coaxially to the axis of elongation; wherein the branch stent is implanted from within a fenestrated stent-graft having oversized fenestrations, the fenestrated stent-graft configured to be first implanted in the main blood vessel at a bifurcation zone including the plurality of branch blood vessels, with each of the oversized fenestrations having respective diameters larger than respective branch blood vessel diameters; wherein the branch stent and the fenestrated stent-graft are together a multi-stent; and wherein the parachute element cover is configured to prevent endoleaks from a main blood vessel blood flow to the aneurysm sac following deployment of the multi-stent. Preferably, the oversized fenestrations are non-customized and are not based on a specific morphology. Most preferably, the fenestrated stent graft has a uni-frame skeleton having a proximal and a distal extension, the proximal and distal extensions not covered with any fabric or polymer. Typically, the extensions are connected to the delivery system by a proximal connection and a distal connection, and wherein the fenestrated stent graft is configured for full control of radial expansion during deployment. Most typically, the delivery and deployment of the multi-stent are part of an endovascular aneurysm repair (EVAR) procedure and wherein the bifurcation zone includes at least one aneurysm chosen from the group including a Juxtarenal Abdominal Aortic Aneurysm (AAA); a Pararenal AAA; and a Suprarenal AAA.

Preferably, the delivery and deployment of the multi-stent are part of the EVAR procedure and wherein the bifurcation zone includes at least one aneurysm chosen from the group including: an Aortic Root Aneurysm; an Aortic Arch Aneurysm; and a Thoracoabdominal Aortic Aneurysm. Most preferably, the delivery and deployment of the multi stent are part of the EVAR procedure and wherein the bifurcation zone includes at least one aneurysm chosen from the group including: an Iliac Artery Aneurysm; and an Internal Iliac Artery Aneurysm. Typically, the delivery and deployment of the multi-stent are sub-procedures of the EVAR procedure, the sub-procedures including a singular insertion and associated withdrawal of the delivery system and components thereof, directed to reduce a chronology of the EVAR procedure.

According to another aspect of the present invention, there is further provided a multi-stent system comprising a plurality of branch stents and an oversized-fenestrated stent-graft, the multi-stent using a delivery system for an intravascular bifurcation zone, the bifurcation zone having a main blood vessel with a main blood vessel and a plurality of side blood vessels, having respective side blood vessel diameters, branching out of the main blood vessel, each of the plurality of branch stents comprising: a tubular element having an unconstrained shape, including: an axis of elongation; a first tubular element end; and a second tubular element end; the tubular element covered with a tubular element cover; and a parachute element having an unconstrained shape, including a substantially flat-toroid/disc configuration, the parachute element having a parachute element cover, the parachute element positioned substantially perpendicularly at the second tubular element end, and the parachute element positioned coaxially to the axis of elongation; wherein each of the plurality of branch stents is implanted from within the oversized-fenestrated stent-graft having oversized fenestrations, the oversized-fenestrated stent-graft configured to be first implanted in the main blood vessel at a bifurcation zone, with each of the oversized fenestrations having respective diameters larger than respective branch blood vessel diameters; wherein the parachute element cover is configured to prevent endoleaks from a main blood vessel blood flow to the aneurysm sac following deployment of the multi-stent.

Preferably, the oversized fenestrations are non-customized and are not based on a specific morphology. Most preferably, the oversized-fenestrated stent-graft has a uni-frame skeleton having a proximal and a distal extension, the proximal and distal extensions not covered with any fabric or polymer. Typically, the extensions are connected to the delivery system by a proximal connection and a distal connection, and wherein the fenestrated stent graft is configured for full control of radial expansion during deployment. Most typically, the delivery and deployment of the multi stent are part of an endovascular aneurysm repair (EVAR) procedure and wherein the bifurcation zone includes at least one aneurysm chosen from the group including: a Juxtarenal Abdominal Aortic Aneurysm (AAA); a Pararenal AAA; and a Suprarenal AAA. Preferably, the delivery and deployment of the multi stent are part of the EVAR procedure and wherein the bifurcation zone includes at least one aneurysm chosen from the group including: an Aortic Root Aneurysm; an Aortic Arch Aneurysm; and a Thoracoabdominal Aortic Aneurysm. Most preferably, the delivery and deployment of the multi stent are part of the EVAR procedure and wherein the bifurcation zone includes at least one aneurysm chosen from the group including: an Iliac Artery Aneurysm; and an Internal Iliac Artery Aneurysm. Typically, the delivery and deployment of the multi stent multi stent are sub-procedures of the EVAR procedure, the sub-procedures including a singular insertion and associated withdrawal of the delivery system or components thereof, directed to reduce a chronology of the procedure.

LIST OF FIGURES

The invention is herein described, by way of example only, with reference to the accompanying drawings, wherein:

FIGS. 3A-3C, 4A-4C, 5A-5C, 6A-6D, 7A-7C are various views (edge, sectional, and isometric) of exemplary branch components, as variations of the exemplary branch component shown in FIGS. 2A-2C, in accordance with embodiments of the current invention;

FIGS. 9A to 9J are schematic diagrams showing a chronology of an endovascular treatment repair of a complex AAA configuration of a typical aortic renal zone configuration, as initially shown in FIGS. 1C-1E, in accordance with embodiments of the current invention—including the branch stent discussed hereinabove in FIGS. 2A-2C, 3A-3C, 4A-4C, 5A-5C, 6A-6D, and 7A-7C, inter alia;

Figures 2A, 2B:
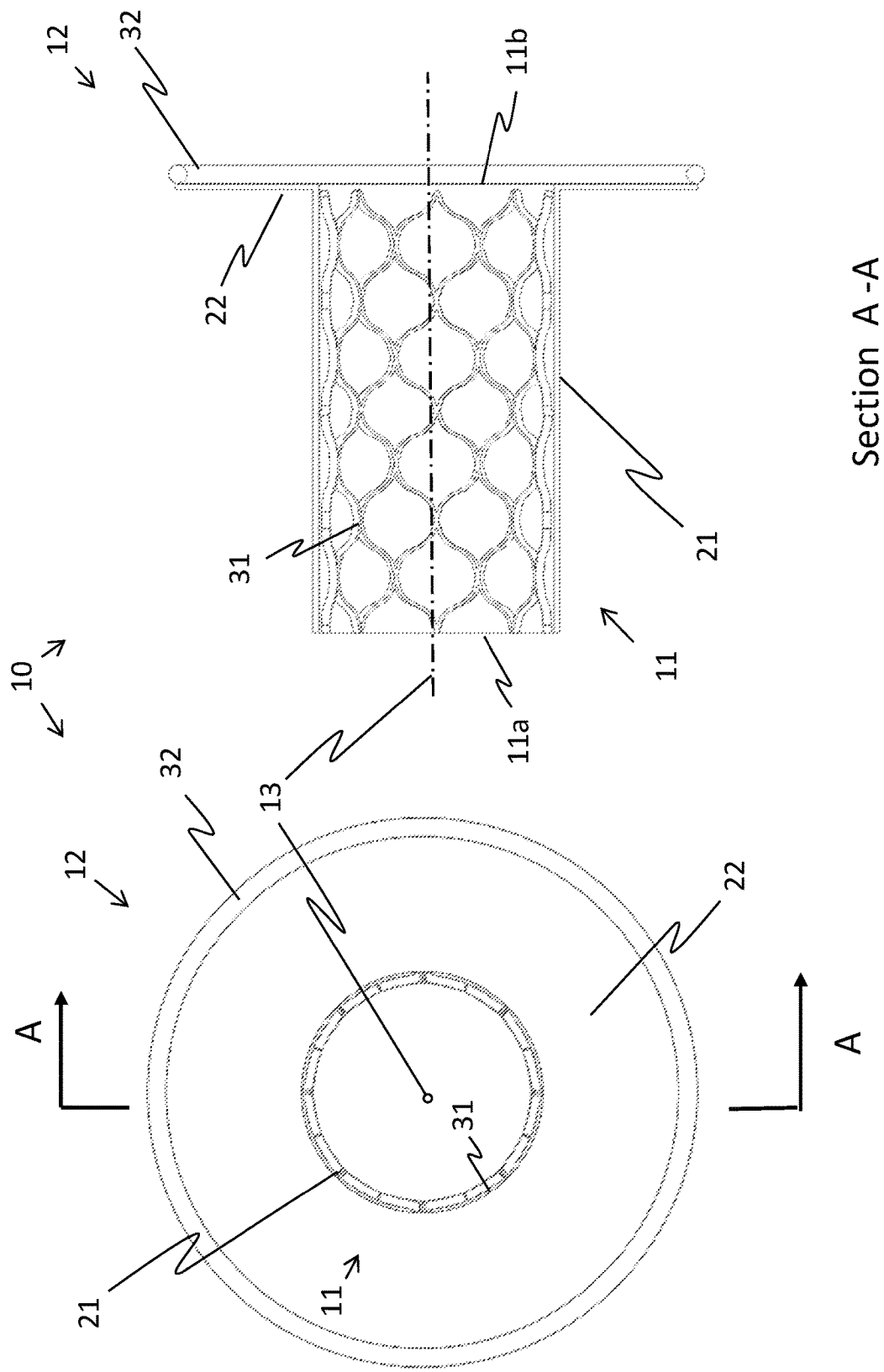
FIGS. 2A and 2B are edge and sectional views, respectively, of an unconstrained exemplary branch component, in accordance with embodiments of the current invention.
Figure 6B:
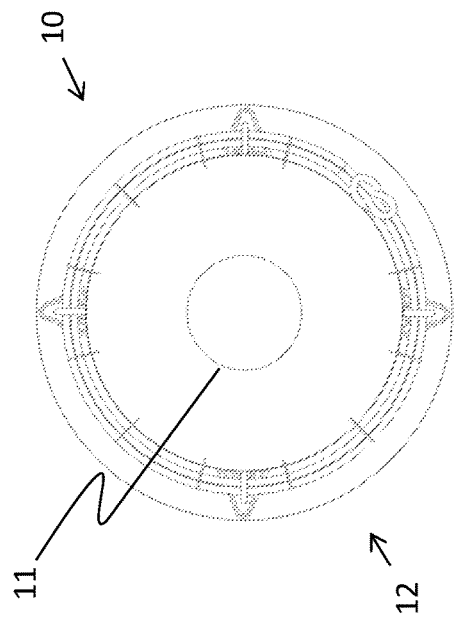
Figure 6D:
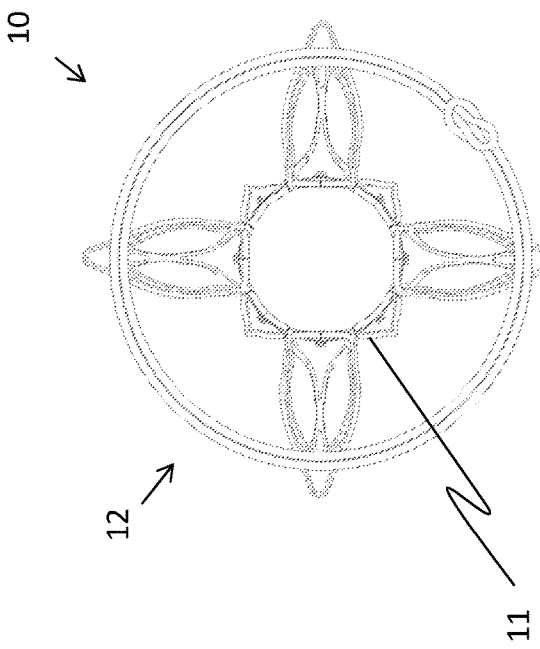
Figure 6A:
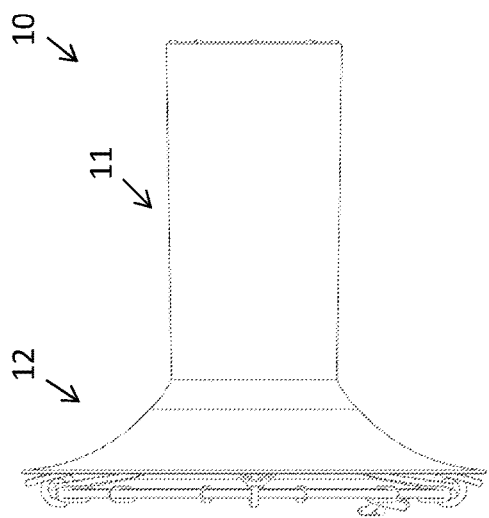
Figure 6C:
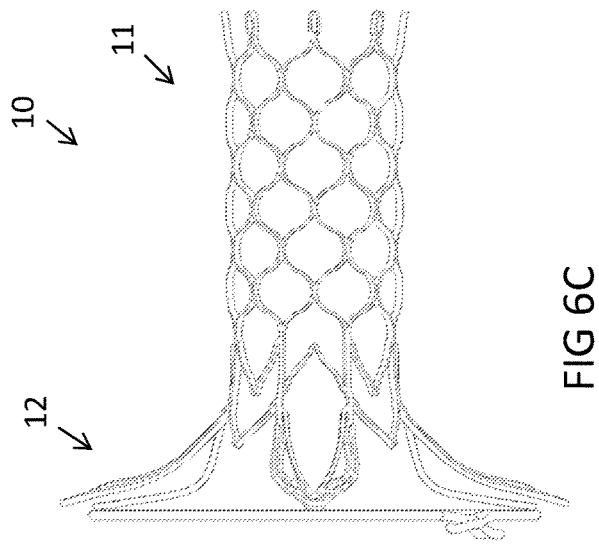
Figure 10A:
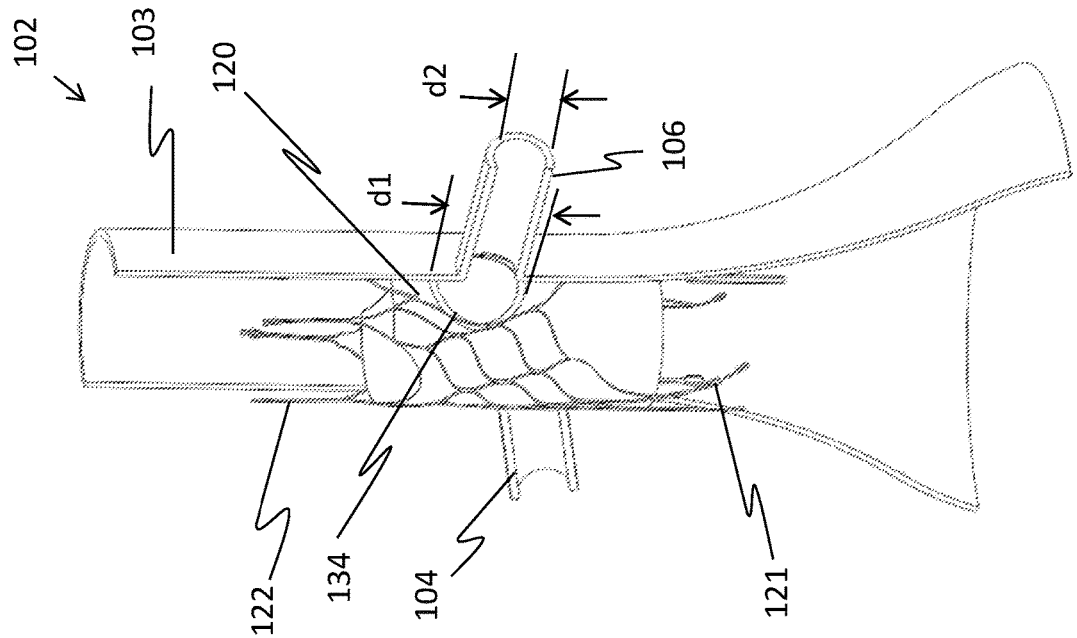
FIGS. 10A and 10B are sectional detailed views of the Juxtarenal AAA configuration as shown in FIGS. 9C and 9D, in accordance with embodiments of the current invention.
Figure 10B:
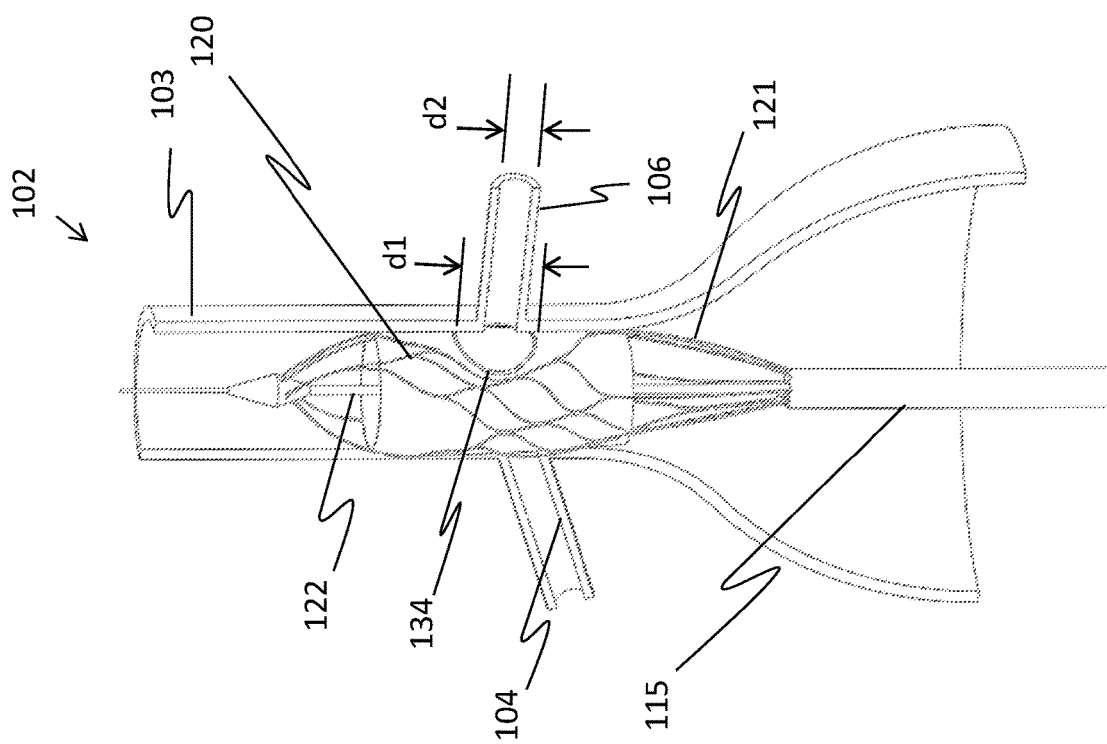
Figure 11B:
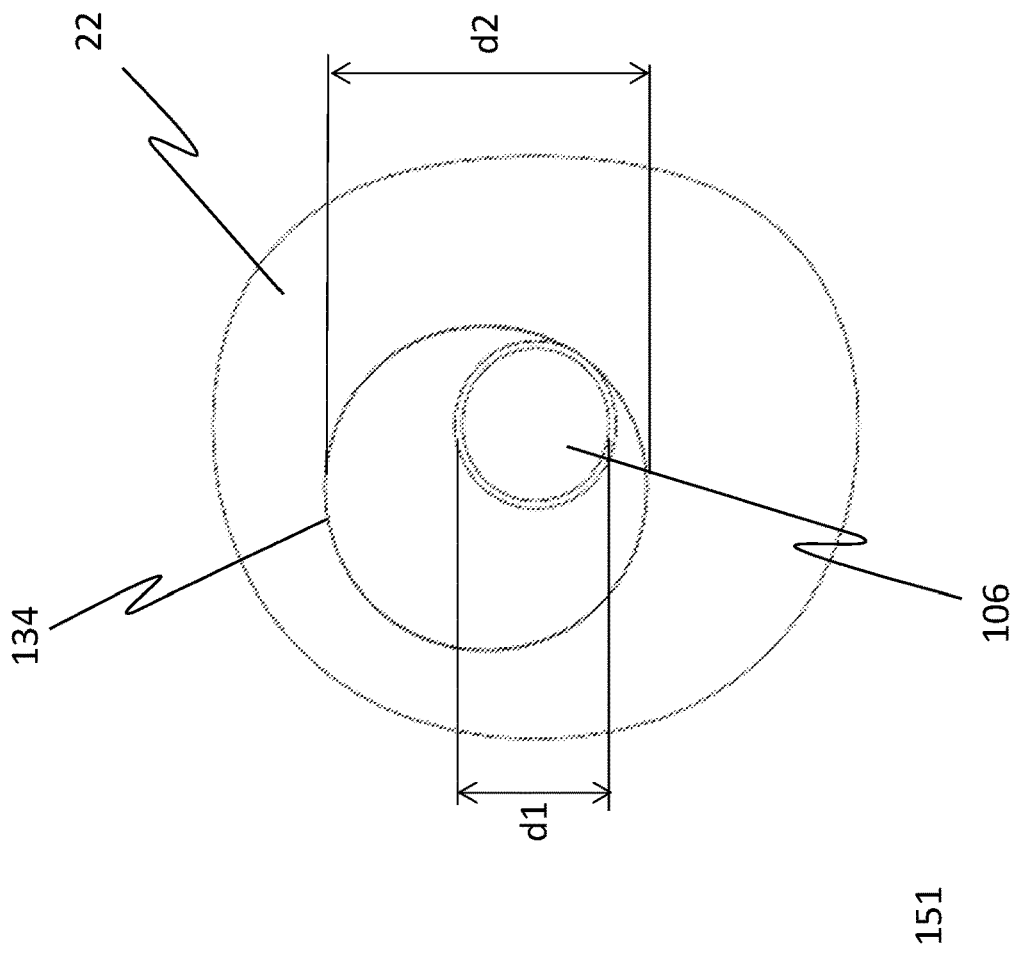
Figure 11A:
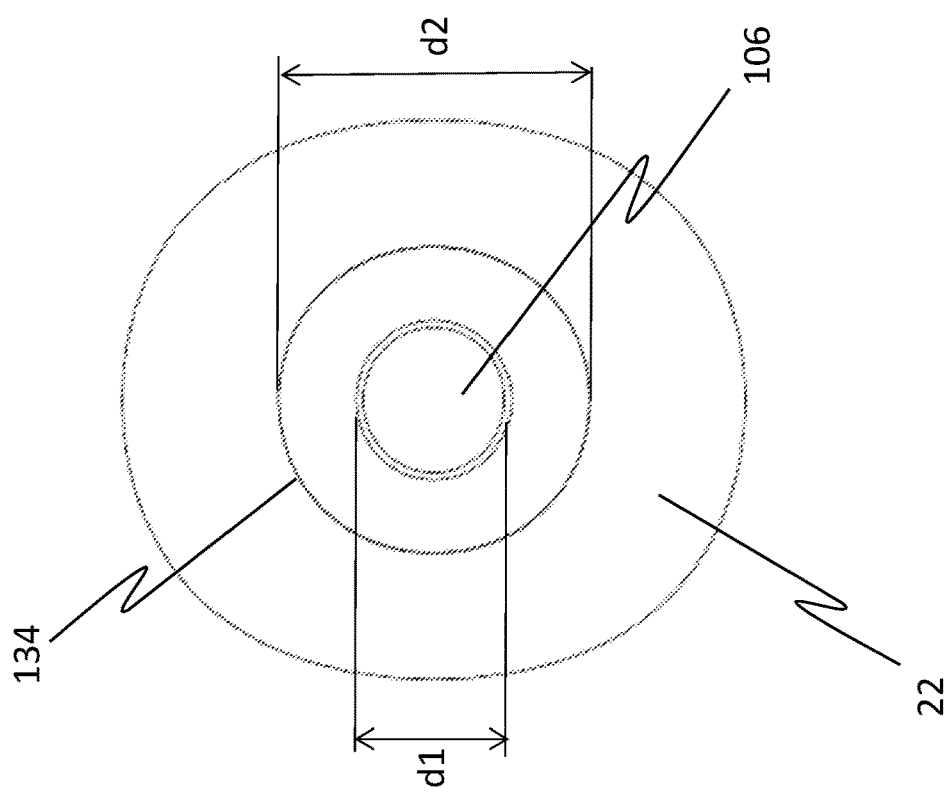
Figure 12B:
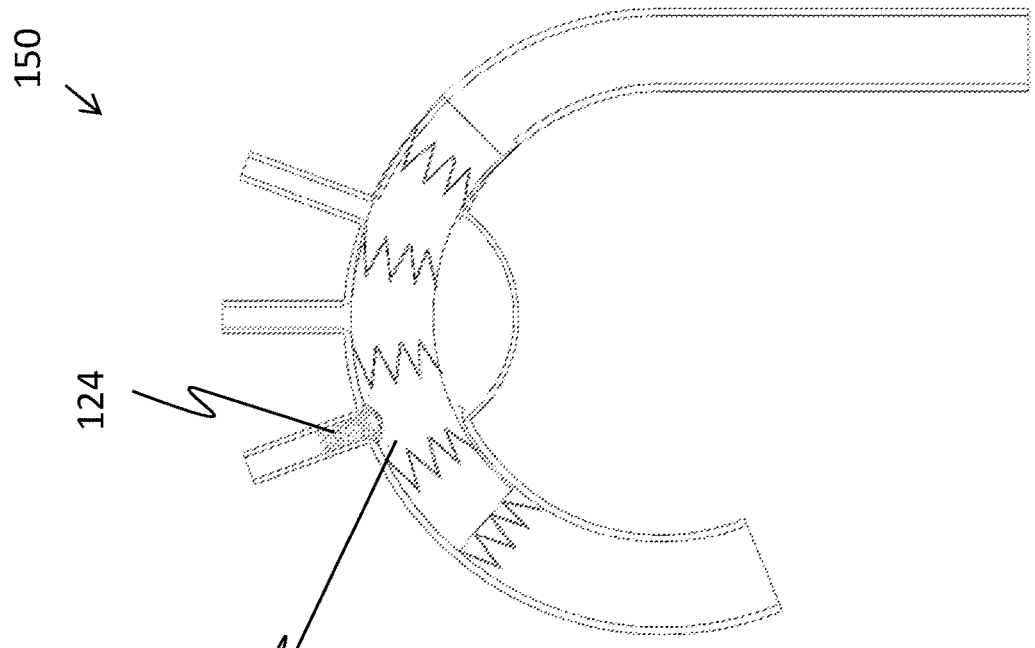
Figure 12A:
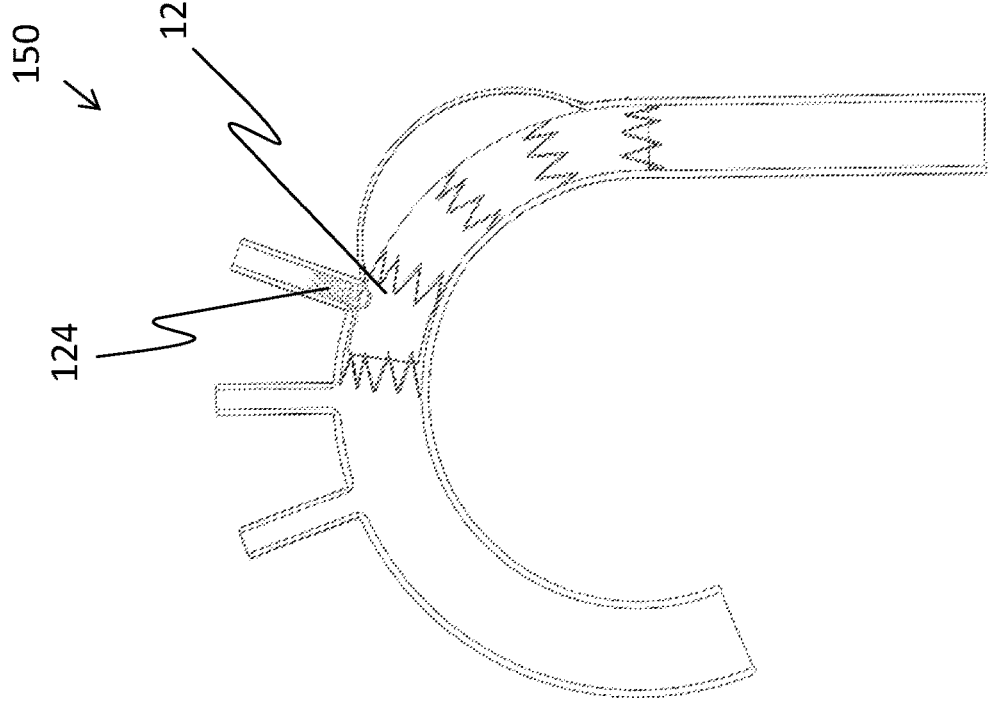
Figure 13B:
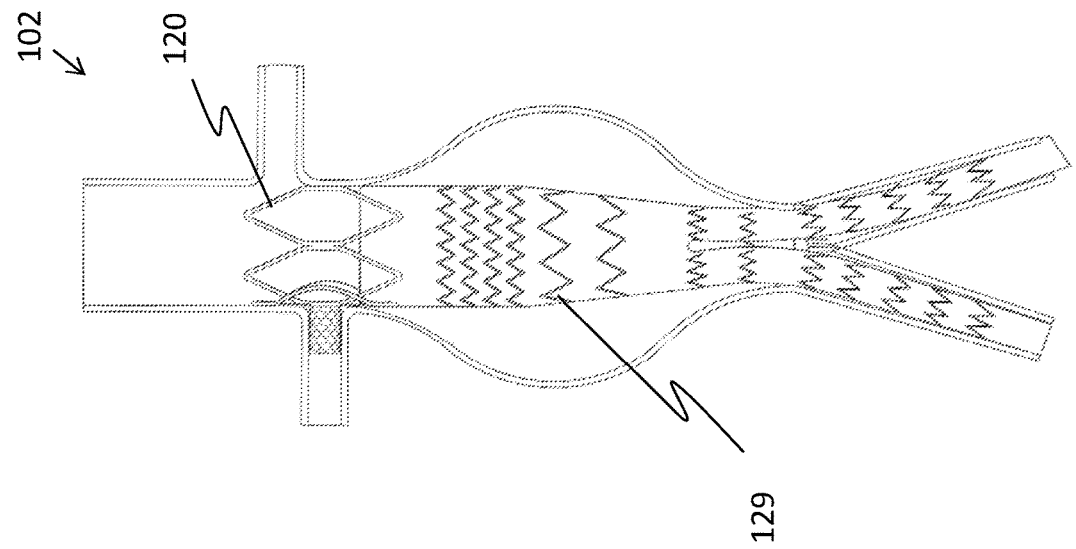
Figure 13A:
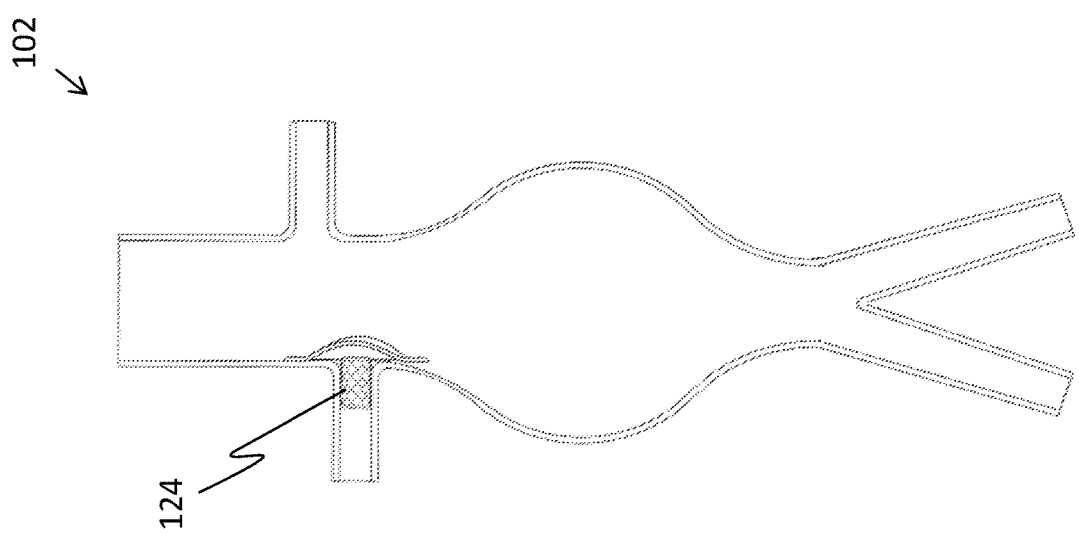

FIGS. 11A and 11B are representations of two alignment configurations of the exemplary oversized fenestration with the second secondary blood vessel, as viewed from within the fenestrated stent-graft, implanted within the primary blood vessel of FIGS. 10A and 10B, with the branch stent of FIGS. 2A, inter alia, deployed and with the parachute element and the parachute element cover thereof likewise deployed, in accordance with embodiments of the current invention;

FIGS. 12A and 12B are schematic representations of aneurysms of an exemplary multi-branch artery, in which the fenestrated stent-graft and the associated branch stents (for example, the first branch stent, inter alia) are implanted, in accordance with embodiments of the current invention;

FIGS. 13A and 13B are schematic representations of the complex AAA short-neck configuration of the typical aortic renal zone configuration, as initially shown in FIGS. 1C-1E, inter alia, in accordance with embodiments of the current invention—including the branch stent discussed hereinabove in FIGS. 2A-2C, 3A-3C, 4A-4C, 5A-5C, 6A-6D, and 7A-7C, inter alia, in accordance with embodiments of the current invention.

Figure 15:
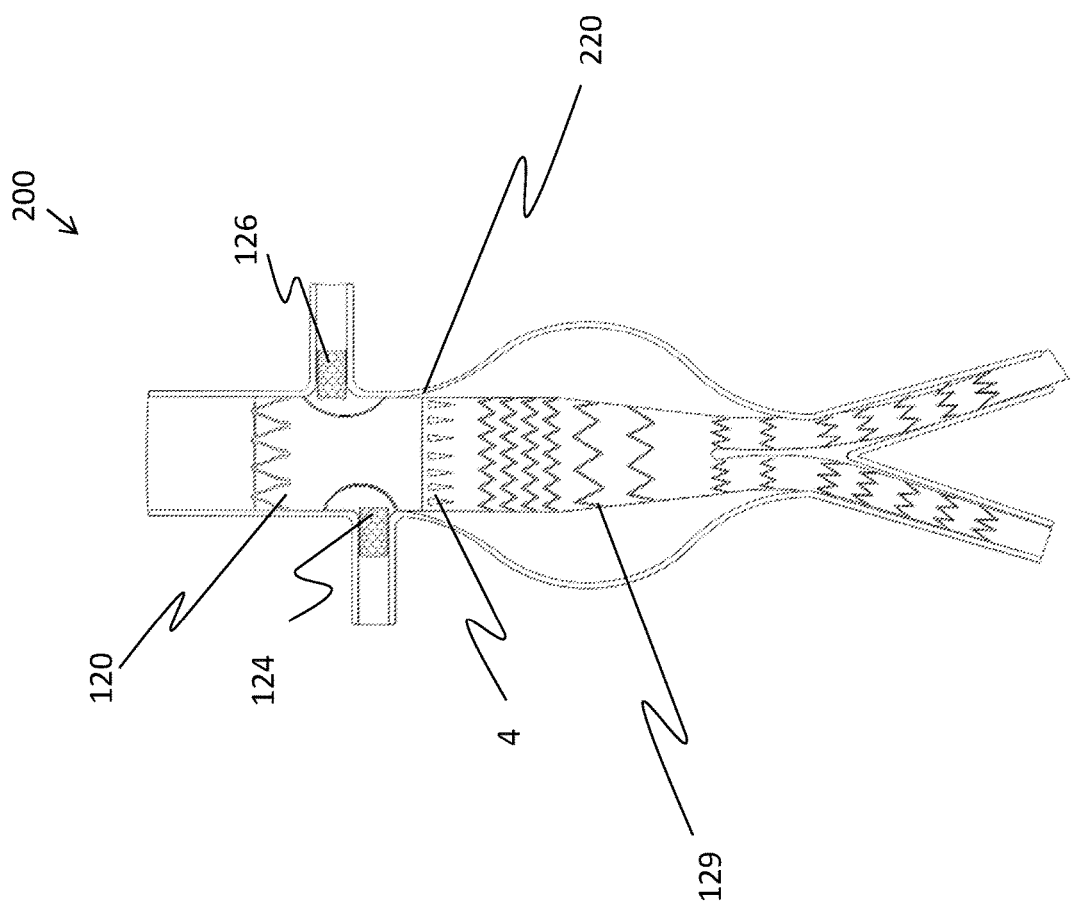

FIGS. 14A and 14B are schematic representations of a typical aortic renal zone configuration showing prior art Type Ia endoleaks;

FIG. 15 is a schematic representation of the AAA typical aortic renal zone configuration, as initially shown in FIGS. 1C-1E and FIGS. 13A-13B, inter alia, with the EVAR implant first implanted into the primary blood vessel and with the suprarenal multi-stent configuration subsequently implanted, in accordance with embodiments of the current invention.

DETAILED DESCRIPTION

Figure 1A:
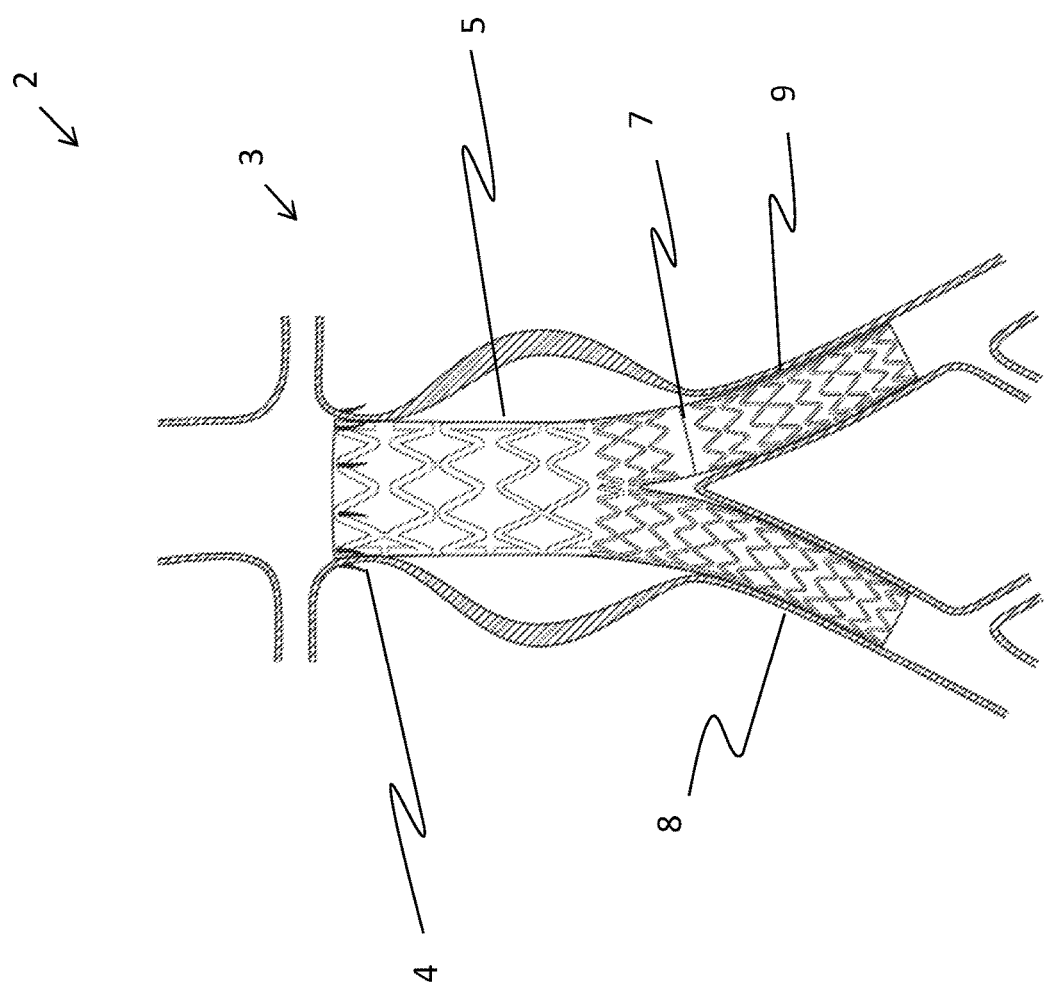
FIG. 1A is a schematic view of a typical aortic renal zone and an endovascular aneurysm (EVAR) repair Prior Art implant.

Reference is currently made to FIG. 1A, which is a schematic view of a typical aortic renal zone having an endovascular aneurysm 3 and a prior art endovascular aneurysm repair (EVAR) implant 3. Prior art implant 3 is characterized by: a plurality of fixation of anchoring barbs 4; a main body 5; a contralateral gate 7; a contralateral limb extension 8; and an ipsilateral limb 9, in treatment of Abdominal Aortic Aneurysms (AAA)—all as known in the art.

Reference is additionally made to FIGS. 1B-1E, which are schematic diagrams of respective morphologies of Infrarenal (1B), Juxtarenal (1C), Pararenal (1D), and Suprarenal (1E) AAA—as known in the art—showing variations (2b, 2c, 2d, 2e) of typical aortic renal zone configuration 2 of FIG. 1A. An "aortic neck" (also referred to hereinbelow as "neck") is indicated by dimension "a", shown in FIGS. 1B and 1C. In prior art Juxtarenal/Suprarenal AAA repair, the presence of an aortic neck is necessary to receive fixation barbs 3 (ref FIG. 1A), which are used to anchor the implant onto the neck and to prevent a Type I endoleak. As such, the variations of typical aortic renal zone configuration corresponding to Juxtarenal, Pararenal, and Suprarenal AAA's are increasingly difficult/improbable choices for such repairs; and these configurations are referred to hereinbelow as a "complex AAA configuration".

Figures 1B, 1C, 1D, 1E:
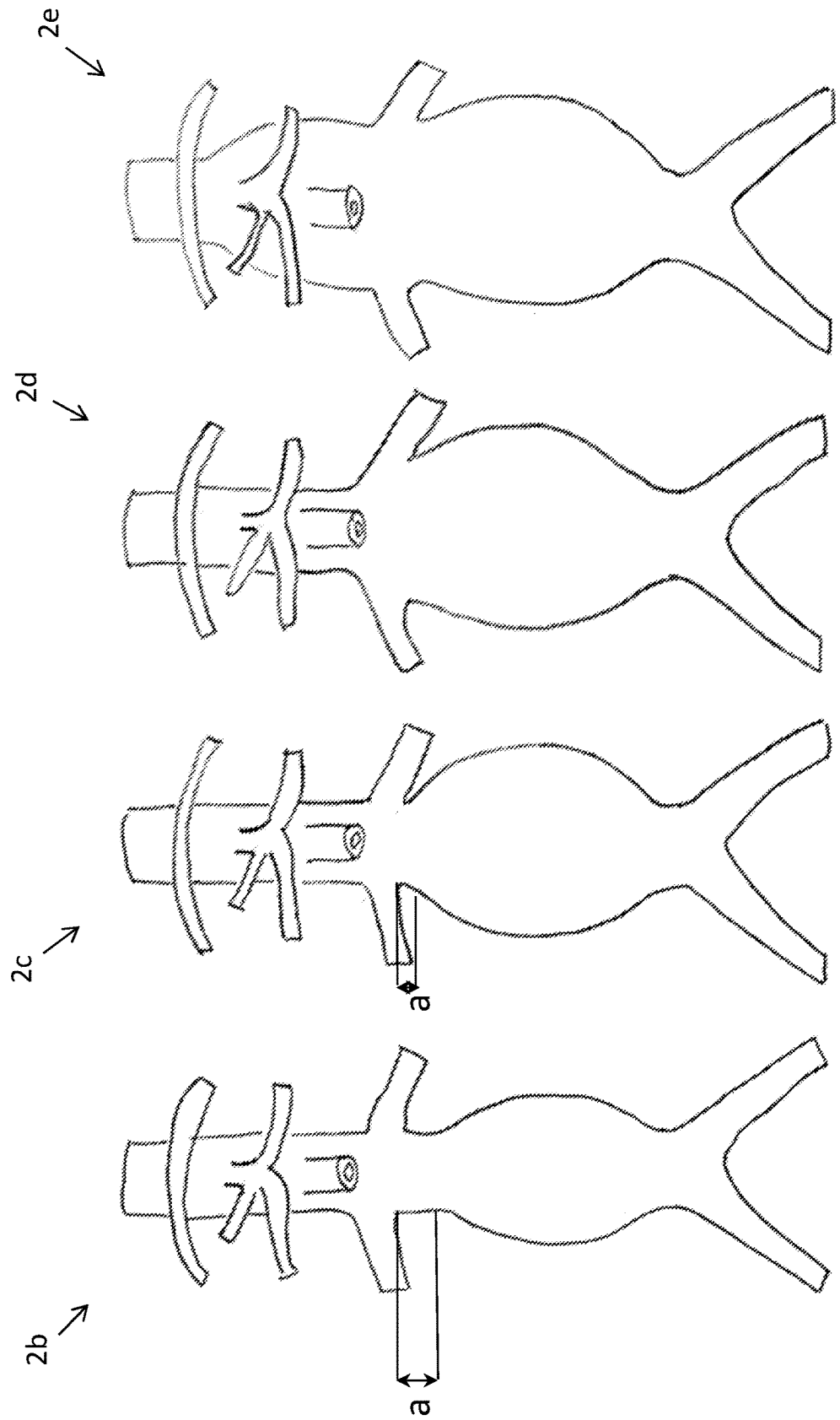
FIGS. 1B-1E are schematic diagrams of respective morphologies of Infrarenal (1B), Juxtarenal (1C), Pararenal (1D), and Suprarenal (1E) AAA—as known in the art—showing variations (2b, 2c, 2d, 2e) of the typical aortic renal zone configuration of FIG. 1A.

Embodiments of the current invention address endovascular solutions for the complex AAA configurations, as shown in FIGS. 1C-1E hereinabove, related to two differing methodologies. One of the methodologies is a patient-dedicated construct, having an aortic stent-graft with fenestration holes for side branch vessels of the vital organs; or a design for a stent-graft having branches for all vital organs; and inserting the stent-graft in advance of the blood flow and producing a connection with the side branch components to vital organ arteries.

The first methodology is related to prior art products such as Zenith® Fenestrated AAA Endovascular Graft and Vascutek Anaconda AAA stent-graft—both as known in the art. In these prior art devices, the stent-graft design is based on specific geometric parameters obtained from a computer tomography (CT) scan that implements drawings of the stent-graft, approved by the attending physician and manufactured to the specific patient. The resultant stent-graft must be inserted very accurately to position it in an exact axial location and with exact alignment of the fenestrated holes to the aortic branch arteries. The procedure calls for a very highly-skilled, expert vascular surgeon. Production of the custom-made fenestrated stent-graft is based on the location of fenestrated holes at the most frequent places stent-grafts usually fail, because of several parameters that influence the design, such as the diameter of holes; a relative distance between holes; and angularity and relative location of the left and right renal, superior mesenteric and celiac arteries.

A second type of methodology is related to prior art products, such as GORE® EXCLUDER® Thoracoabdominal Branch Endoprosthesis and Medtronic Valiant Navion™ Thoracic Stent Graft System, as known in the art. These types of stent-grafts are "off-the-shelf" and are scaled with different sizing depending on a specific patient's aortic diameter.

The second methodology includes performing a connection to the four arterial branches: the left and right renal, superior mesenteric, and celiac arteries. This second methodology is not an optimal solution for most patients, as it cannot cover a large range of complex AAA configurations not involving all four branch arteries. Difficulties include not only increased cost and procedure chronology, but an increased number of post-implantation complications, such as Type IIIb endoleaks, stent fractures, and stent ring enlargements.

In U.S. Pat. No. 10,076,433 ('433 patent) whose disclosure is incorporated by reference, Bernshtein, the Inventor of the current patent application, discloses a multi stent delivery system for intravascular bifurcation zone delivery and deployment of a multi stent, the bifurcation zone having a main blood vessel, the main blood vessel having a main blood vessel longitudinal axis and at least one side blood vessel inclined/branching out of the main blood vessel, the delivery system comprising: a catheter having a catheter longitudinal axis substantially coaxial with the main blood vessel longitudinal axis, a tube positioned coaxially within the catheter, the catheter having a distal end and a proximal end, and the tube containing: at least one crimped side stent for deployment substantially normal to the catheter longitudinal axis and into the side blood vessel; and at least one crimped main stent for deployment substantially along the catheter longitudinal axis into the main blood vessel; wherein the at least one crimped side stent and at least one crimped main stent are part of a unified/singular configuration within a sheath, located substantially at the distal end. '433 includes novel solutions related to EVAR and FEVAR considerations.

Embodiments of the current invention include a paradigm shift over prior art/existing methodologies using a connecting component from a fenestrated or branched stent graft, implanted in in a main blood vessel, to a branch blood vessel therefrom by choosing a typical off-the-shelf fenestrated stent graft that is fitted with a diameter and a length to the target main and branch blood vessels. The current invention proposes a paradigm shift from that where the component connecting between branch vessel to the fenestrated stent graft is specifically designed for the dedicated procedure. The "branch component" of embodiments of the current invention allows for an overall simplified procedure; the component being produced as an off-the-shelf product, thereby serving to increase the number of patients that are suitable for endovascular treatment.

Reference is currently made to FIGS. 2A and 2B, which are edge and sectional views, respectively, of an unconstrained, exemplary branch component 10, in accordance with embodiments of the current invention. Exemplary branch component 10 (otherwise referred to as "branch-stent" hereinbelow) includes two major elements: a tubular element 11 (shown in the figure in a deployed configuration), having a first end 11a and a second end 11b, the tubular element having an axis of elongation 13, and a parachute element 12. Parachute element 12 (shown in the figure in an unconstrained configuration) has a substantially flat-toroid/disc configuration, with the parachute element positioned substantially perpendicularly at the second end 11b and positioned coaxially to axis of elongation 13, as shown in the figure. Tubular element 11 is covered with a tubular element cover 21 and parachute element 12 is covered with a parachute element cover 22. Respective element covers may be similar or may be different for respective elements 11 and 12. Covers 21 and 22 may be fabricated of materials such as, but not limited to: a fabric; a polymer; silicon, sutures; wires; a metallic or rubber connector; and other flexible material that may be crimped to a catheter and reshaped/expanded following deployment. When the branch stent is fully deployed in situ, parachute element cover 22 serves to prevent endoleaks from aortic blood flow to the aneurysm sac, as described further hereinbelow.

The tubular element has a tubular stent 31, typical of most stents as known in the art. The tubular stent may be adapted for balloon deployment or self-deployment configuration. For balloon deployment, tubular stent 31 is fabricated from materials such as, but not limited to stainless steel and cobalt-chrome alloys. For self-deploy methodology, tubular stent 31 is produced from smart memory alloys, such as but not limited to nitinol and nitinol alloys.

The parachute element includes a reinforcement element 32 which serves to maintain an initial flat shape and provide a deployed shape (not shown in the current figures). Reinforcement element 32 may take the form of an exemplary wire ring (as shown in the FIGS. 2A and 2B); spring-like shapes; stent-like metallic structures; and additional metallic extensions of the tubular element, inter alia. A requirement for the reinforcement element is that it may be crimped to a cylindrical shape into a catheter and to regain a flat shape in an initial deployment stage, as described further below.

Parachute element cover 22 is preferably connected to reinforcement element 32 with a suture. Optionally or alternatively, the parachute element cover is fabricated as one piece by electrospinning or other coating techniques, as known in the art. The center of the parachute element has a hole, which is aligned substantially coaxially with axis of elongation 13, to allow substantially unimpeded blood flow through the center of the parachute element (and thereby through the branch stent) when the branch stent is deployed at a bifurcation, as further described hereinbelow.

Although the shape of reinforcement element 32 shown in the current figure is substantially that of a radial shape, the reinforcement element may have an elliptical, a square, a rectangular, a spring-like, and a loop-like shape, having a closed or unclosed loop structure, as noted further hereinbelow. Additionally, whereas tubular element 11 and parachute element 12 are aligned coaxially with regard to axis of elongation 13, as described hereinabove, respective alignment of both elements need not necessarily be concentric to axis of elongation 13. In other words, there may be an optional and/or alternative offset of either tubular element 11 and/or parachute element 12 with regard to a concentric alignment with the axis of elongation. (Such an alignment/offset is not shown in the current figures.)

As further discussed hereinbelow, in an unconstrained configuration tubular element 11 typically has a diameter value smaller than that of parachute element 12, thereby allowing easier insertion of branch-stent 10 into a branch vessel during the procedure. Additionally, when tubular element 11 has a crimped diameter value smaller than that of parachute element 12, such a configuration ensures that the branch-stent is not introduced too deeply into the branch vessel, because of a "mechanical stopper" effect of the configuration, as further described hereinbelow. Parachute element 11 may contain barbs or other fixation elements, as known in the art. Additionally or optionally, the tubular element and the parachute element may be crimped to substantially the same diameter values.

Branch stents are typically introduced through fenestrated holes of a stent graft, otherwise known as an aortic stent, as known in the art. In embodiments of the current invention, respective diameters of the oversized fenestrations are larger than respective diameters of the branch vessels, thereby enhancing alignment tolerance for deployment with a majority of patients and thereby allowing flexibility and more suitability to a wider range of patient morphologies. It is clear that this consideration becomes even more important as the number of branch vessel arteries increases from 1 to 2 or more. The branch stent may therefore be an off-the-shelf product for treatment of AAA aneurysms.

Reference is currently made to FIGS. 3A-3C, 4A-4C, 5A-5C, 6A-6D, 7A-7C, which are various views (edge, sectional, and isometric) of exemplary branch components, as variations of the exemplary branch component shown in FIGS. 2A-2C, in accordance with embodiments of the current invention. Apart from the differences described below, exemplary branch component 10, tubular element 11, and parachute element 12 of FIGS. 2A-2C (hereinabove) are identical in notation, configuration, and functionality to that shown in FIGS. 3A-3C, 4A-4C, 5A-5C, 6A-6D, 7A-7C, and elements indicated by the same reference numerals and/or letters are generally identical in configuration, operation, and functionality as described hereinabove.

FIGS. 3A-3C show variations of the branch stent for an alternative shape of the parachute element with reinforcement element 32 (ref FIGS. 2A-2C) as a wire with a loop on the opposite sides of the reinforcement element, all shown in an unconstrained configuration. The shape of the reinforcement element seen in FIGS. 3A-3C allows for an increased deployment force and adaptation for the vessel morphology, while concomitantly presenting a smaller crimp profile in comparison to the reinforcement element presented in FIGS.

2A-2C. It is additionally noted that the parachute element presented in FIGS. 3A-3C has an unconstrained cylindrical curvature characterized by a radius that is larger than the radius of the primary blood vessel (i.e., the blood vessel wherein the fenestrated stent graft is configured).

FIGS. 4A-4C show variations of the branch stent having an alternative shape of parachute element 12, having an inner parachute element cover 22a, defined by an inner reinforcement element 32a, in addition to parachute element 22 defined by reinforcement element 32, as described in previous figures hereinabove. The current configuration allows for two distinct parachute element covers having respective curvature and respective materials, both of which may be varied as necessary to form an optimal parachute element shape to improve the functioning of the branch stent versus hemodynamics from the main blood vessel to the branch vessel and vital organs.

FIGS. 5A-5C show an alternate crimping configuration of the branch stent shown in FIGS. 2A-2B, including crimping of the branch component into a catheter 40. The tubular and the parachute elements are crimped co-axially within the catheter a shown in FIGS. 5A and 5B, whereas FIG. 5C shows a crimped configuration of the branch stent, without the catheter.

FIGS. 6A-6D and FIGS. 7A-7C show alternate branch stent configurations, in unconstrained views, including a scaffolded-type parachute element having additional reinforcement elements. The current structure/configuration serves to increase the robustness of the branch stent and to further stabilize the connection of the branch stent to the aortic stent-graft.

The parachute element shown in FIGS. 6A-6D, serves to fix the branch stent in position from both sides of the fenestrated stent graft, i.e., inside and outside.

In FIGS. 7A-7C, the parachute element is configured from a flat sheet having fixation barbs 42, which may serve to ensure prevention of post-implantation endoleaks.

Common to all the variations of the exemplary branch component configurations shown in FIGS. 2A-2C, 3A-3C, 4A-4C, 5A-5C, 6A-6D, and 7A-7C, are the following:
- self-sealing configuration by the parachute element of the branch stent, following deployment from the primary blood vessel, thereby enabling a seal of the primary blood vessel relative to the secondary blood vessel, and obviating a need for additional connection/barb elements;
- concomitant easier alignment and insertion of the branch stent into the secondary blood vessel;
- unique configuration/construction, allowing compact branch stent crimping to a substantially flattened and/or curved shape without excessive mechanical stress/strain on the branch stent, to present a significantly reduced cross-section within a sheath/catheter and within a delivery system—as detailed further hereinbelow;
- self-expansion—meaning, once the crimped branch stent is deployed from the delivery system the branch stent can open on its own; without the need for a balloon and/or other deployment mechanisms;
- balloon-expansion—meaning the crimped branch stent may be deployed by balloon dilatation;
- controlled expansion—meaning the deployed branch stent, in addition to being self-expanding and or balloon-expanding is nonetheless controlled as it expands—as detailed further hereinbelow;
- construction from metallic (such as smart memory alloys) and/or plastic materials, as known in the art; and
- may be incorporated with a main, larger stent/stent-graft (as described further hereinbelow), thereby allowing deployment of one or more secondary/branch stents, along with the main stent, thereby yielding a reduced procedure chronology—as detailed further hereinbelow.
- in virtually all configurations, the branch component serves only as a geometric adaptation to the fenestrated stent-graft without rigid fixation; thereby allowing to the branch component not to be subject to drag forces of the stent-graft (due to blood flow) and thereby obviating post-implantation fractures of the tubular element.

In all of the variations of the branch stent, tubular element 11 is crimped radially, and parachute element 12 has either two crimped elbows and/or is rolled. Each element may be crimped to a different diameter. The independent design of the two elements and their connection only with flexible fabric, increases the flexibility of the catheter's sheath, allowing enhanced maneuverability, especially at the entrance to blood vessel branches.

Figure 8A:
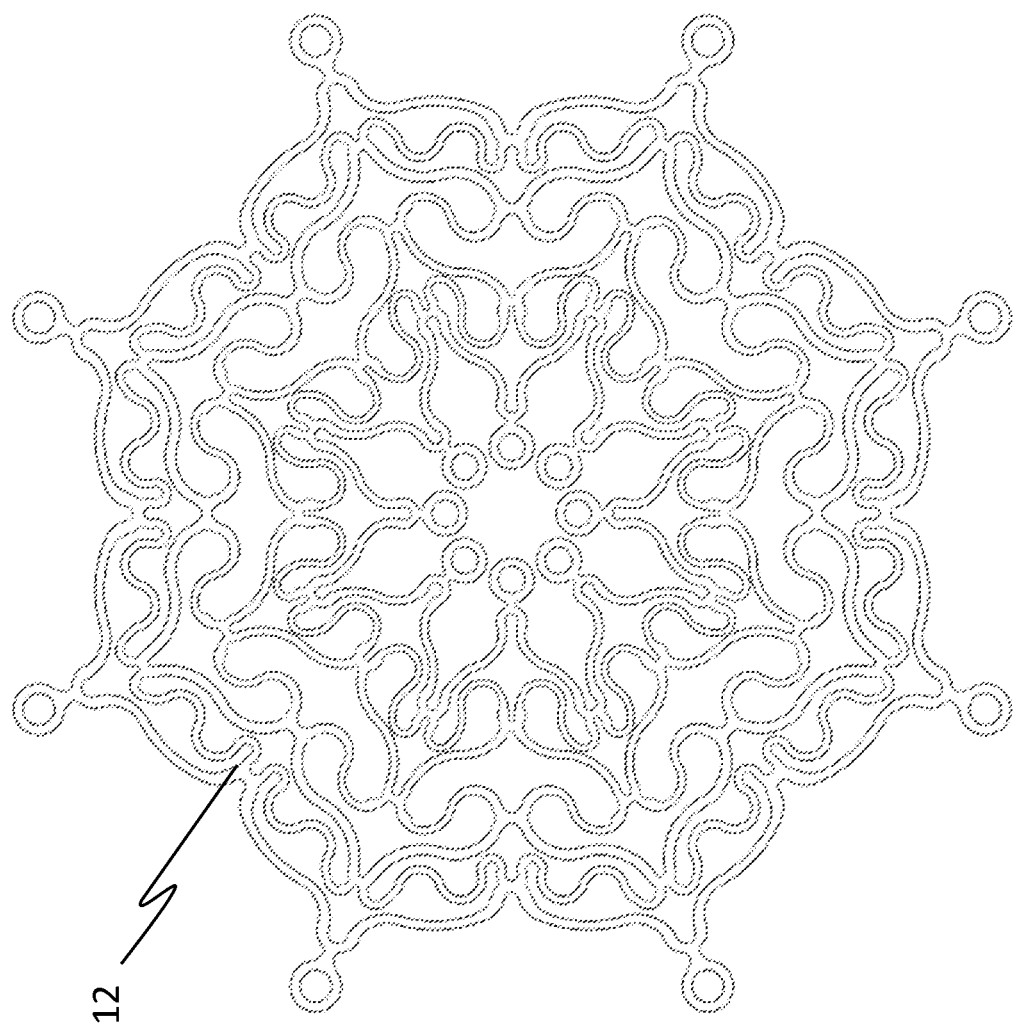
FIGS. 8A and 8B are unconstrained and crimped side views, respectively, of the parachute element as variations of the parachute element shown in FIGS. 2A-2C, in accordance with embodiments of the current invention.
Figure 8B:
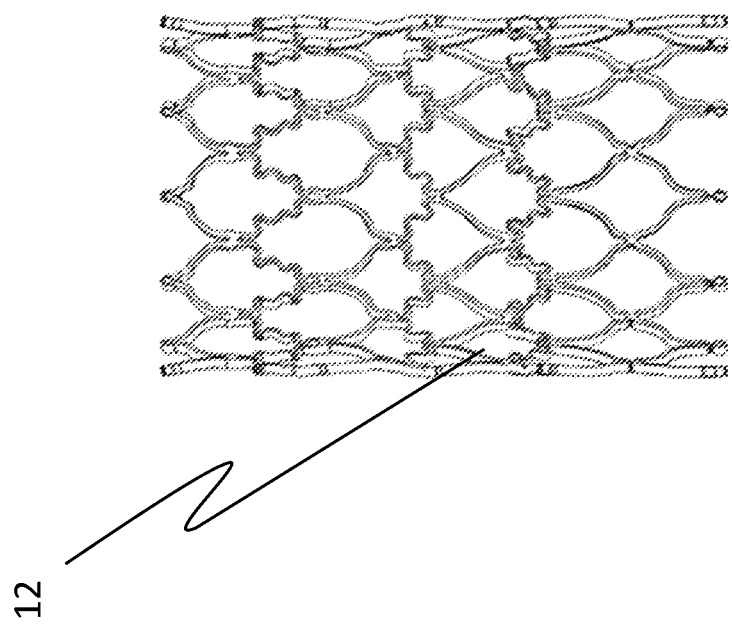

Reference is currently made to FIGS. 8A and 8B, which are unconstrained and crimped side views, respectively, of the parachute element as variations of the parachute element shown in FIGS. 2A-2C, in accordance with embodiments of the current invention. Apart from the differences described below, parachute element 12 of FIGS. 2A-2C (hereinabove) is identical in notation, configuration, and functionality to that shown in FIGS. 8A and 8B, and elements indicated by the same reference numerals and/or letters are generally identical in configuration, operation, and functionality as described hereinabove.

Reference is currently made to FIGS. 9A to 9J, which are schematic diagrams showing a chronology (i.e., stages of a procedure) of an endovascular treatment repair of a complex AAA configuration of a typical aortic renal zone configuration 102, as initially shown in FIGS. 1C-1E, in accordance with embodiments of the current invention—including the branch stent discussed hereinabove in FIGS. 2A-2C, 3A-3C, 4A-4C, 5A-5C, 6A-6D, and 7A-7C, inter alia.

Figure 9B:
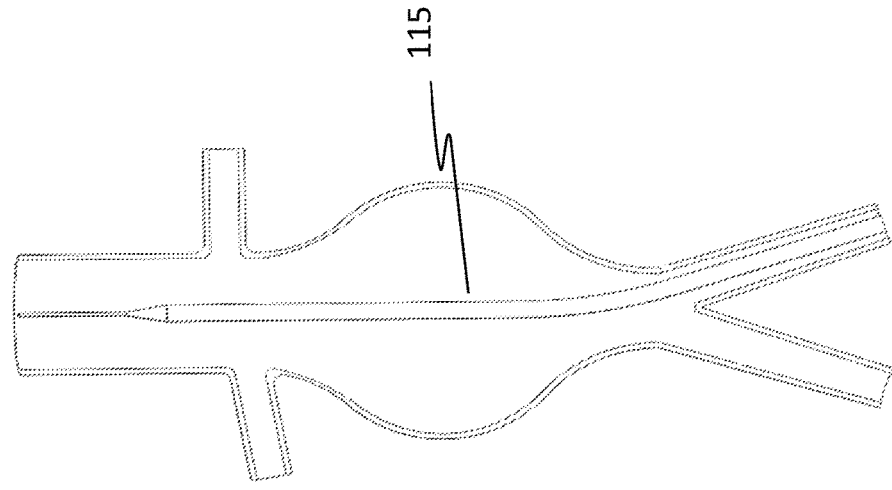
Figure 9A:
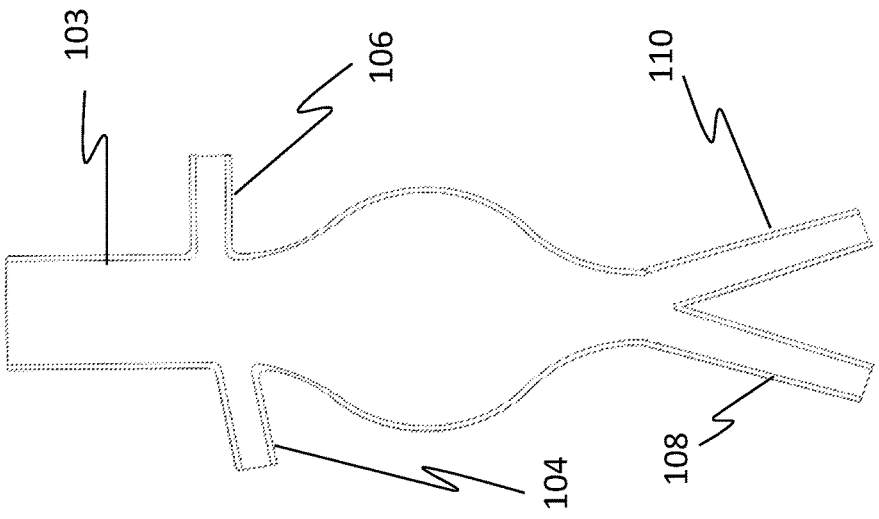

FIG. 9A shows a Juxtarenal AAA configuration 102 (i.e., "a complex AAA configuration", as noted hereinabove) having a short neck ("a", as identified in FIGS. 1B-1E), which cannot be treated with traditional AAA stent-grafts. Configuration 102 includes a primary blood vessel 103 (also referred to hereinbelow as an "aortic vessel"); a first secondary blood vessel 104; a second secondary blood vessel 106; an iliac blood vessel 108; and a femoral blood vessel 110—all as known in the art. For simplicity in the following figures, elements 103, 104, 106, 108, and 110 are not included in configuration 102 shown in FIGS. 9B-9K.

Stages of the endovascular treatment repair initially proceed as disclosed in the «433 patent, namely an endovascular approach is performed through either or both of the femoral and iliac vessels with an introducer sheath/catheter/guide wire 115, as shown in FIGS. 9B and 9C. Sheath/catheter/guide wire 115 is additionally referred to hereinbelow as the "delivery system". Delivery system 115 is a common term for various catheter and/or guide wire configurations used throughout the chronology shown in FIGS. 9B-9K.

A fenestrated suprarenal stent graft 120 is introduced using the delivery system, as shown in FIG. 9C. Fenestrated suprarenal stent-graft 120 is positioned in a suprarenal zone, which is also referred to as a "bifurcation zone". It should be noted that in embodiments of the current invention, fenestrated suprarenal stent graft 120 may be a standardized stent graft—and not a customized stent graft—having "oversized fenestrations"—meaning fenestrations which are non-customized, and which are typically larger than the diameter of the secondary blood vessel, as further described hereinbelow.

Based on fluoroscopy markers of the fenestrated suprarenal stent-graft and delivery system/sheath, the stent-graft is positioned at an optimal axial and rotational position in the supernal zone and at an approximate alignment position of the fenestrations relative to openings of the branch vessels. At this stage, preliminary deployment of the stent-graft is performed, while the stent-graft remains connected to the delivery system. Using fluoroscopy and contrast fluid checking, an exact alignment of the stent-graft fenestrations to the branch vessel openings is accomplished—all as shown in FIG. 9C.

In prior art techniques, such as in FEVAR, definition of the target vessel location and deployment of the fenestrated stent graft are performed based solely on the axial and rotational orientation radiopaque markers. After the fenestrated stent-graft is partially deployed, dislocation of the stent-graft is very difficult, and for small aortic diameters it is completely impossible. Additionally, after deployment of the fenestrated stent-graft, the renal arteries have a plurality of assistance catheters therein, which must be retracted and be reinserted through the fenestrations of the stent-graft into the renal arteries. The maneuver of retraction and reinsertion demands extremely high expertise by the vascular surgeon or interventional radiologist performing the procedure, and it requires an additional iliac approach for the assistance catheters and fluoroscopy, yielding an overall subsequently long chronology. In embodiments of the current invention, such as demanding maneuver is obviated—as described hereinbelow.

The location of the renal arteries may be allocated with an assisted angio catheter approach through one of the aortic arch branch vessels, such as: brachiocephalic; left common carotid; or left subclavian arteries and allocated above the aortic suprarenal zone. As noted hereinabove, embodiments of the current invention include oversized fenestrations of the stent-graft, wherein the oversized fenestrations are much larger than typical FEVAR stent graft fenestrations/holes (which are typically designed in customized fashion, based on the specific patient's morphology and which require a tight location tolerance).

As shown schematically in FIG. 9C, fenestrated suprarenal stent-graft 120 may be designed from a uni-frame skeleton, which is covered with fabric or polymer material from the inside. The uni-frame skeleton may have extensions, which are connected to the delivery system by a proximal connection 121 and a distal connection 122. With both sides of the fenestrated stent graft, having connections of the frame to the delivery system, several important goals are achieved:

Firstly, having connections on both proximal and distal sides, full control of deployment is achieved. Not only are the axial and rotational positions of the fenestrated holes of the stent-graft fully controlled, but additionally, radial expansion of the stent-graft during deployment is also fully controlled. This point is important for smaller aortic diameters, typically those of women and patients of Asian origin, who are ineligible for prior art FEVAR and Chimney endovascular treatments.

The partial deployment of the fenestrated stent-graft does not interfere with the blood flow through the aorta and vital organs branch vessels, because the frame's proximal and distal bare extensions are not covered with any fabric or polymer.

Additionally, branch vessels are not currently occupied with target catheters during the procedure, thereby allowing direct landing of holes (i.e., fenestrations) over the branch vessels openings, and a simultaneous checking of the exact location of the holes using fluid contrast from the external angio catheter. The angio catheter may be located not just above the suprarenal area but may be moved closer to the renal openings during partial deployment of the stent graft to ensure sufficient blood flow through the renal arteries.

The frame of the fenestrated stent-graft design as a series of closed cells pattern allows not only control of the location of the holes (as described above) but also allows recapturing of the device and repositioning, including fully retrieving the fenestrated stent-graft back into the delivery system and removal from the body, if necessary. Such would be the case when, following partial deployment, the physician did not succeed to align/allocate the fenestrated holes over the branch vessels openings.

The design of the stent graft, in addition to oversized fenestrations, may include slots or holes that allow natural blood flow to the superior mesenteric artery and/or celiac axis.

Alternatively or optionally, embodiments of the current invention may include a stent-graft with oversized fenestrations (as described above)—but without extensions, such as proximal connection 121 and distal connection 122 (not shown in the current figures).

The distal side of the frame of fenestrated suprarenal stent-graft 120 may include anchoring barbs (not shown in the figures), which are fully crimped near the tip of the catheter during partial deployment of the stent graft, and after full deployment may perform penetration of the aorta to ensure anchoring and to prevent post-implantation migration.

When the preliminary deployment is performed correctly, the fenestrated stent-graft is released from the delivery system and the delivery system is withdrawn from the aortic renal zone, as shown in FIG. 9D. If preliminary deployment is not performed correctly (i.e., not as expected, and with misalignments of the fenestration holes to openings of the branch vessels) the stent-graft is manipulated by the delivery system to affect changes in axial and rotation configuration, as described hereinabove. Manipulation/correction may be repeated several times until an optimal position of the stent-graft concerning the branch vessels is obtained (FIG. 9D).

Figure 9G:
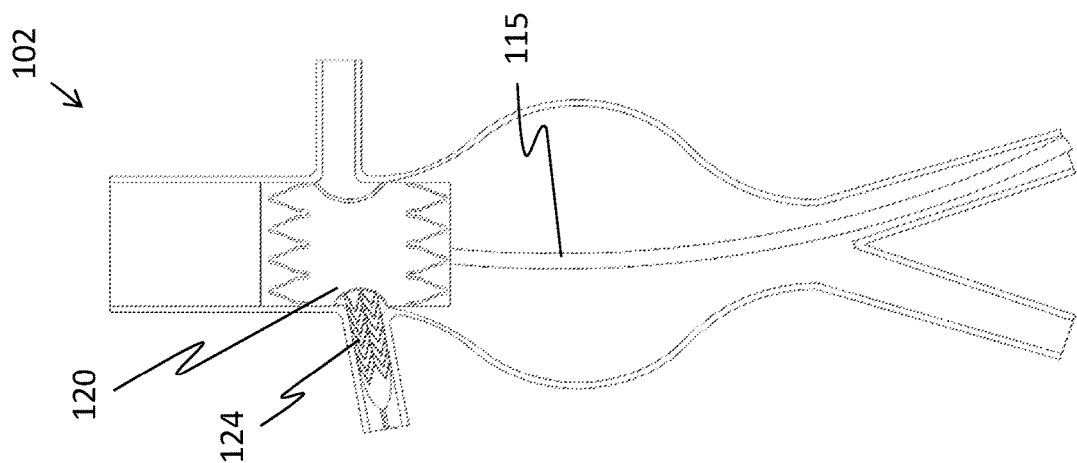
Figure 9F:
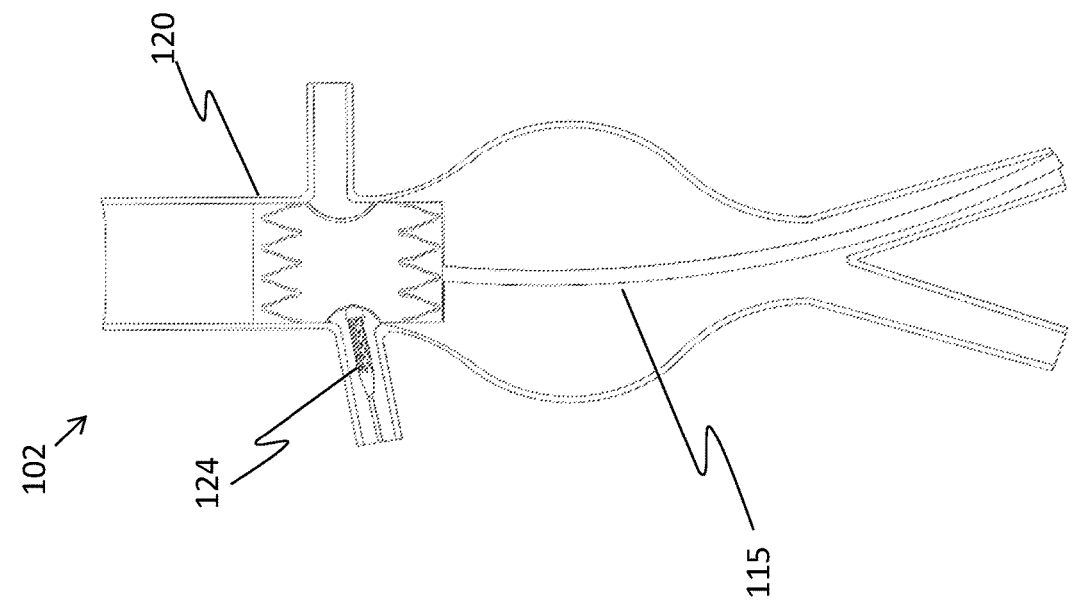
Figure 9E:
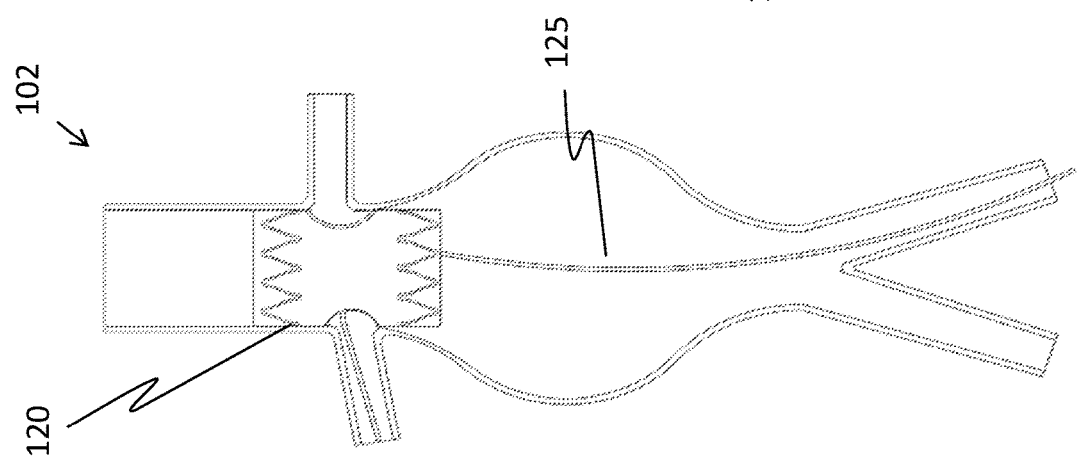

Referring to FIGS. 9E and 9F, through a trans-femoral approach, a guidewire 125 is first inserted into the branch vessel, followed by the introduction of the delivery system 115 with a first branch stent 124 (shown in a crimped configuration) into the branch vessel, through the fenestrated hole in the stent-graft.

In FIG. 9G, first branch stent 124 is deployed, including deployment of the tubular element, followed by deployment of the parachute element. (Note that the parachute element is deployed from within the stent graft and that the parachuter element is therefore not visible in the figures.) Deployment of the tubular element proceeds as noted hereinabove (i.e., balloon dilatation, self-expandability, etc.) Following tubular element deployment, the parachute element is deployed, based on an elastic spring-effect and self-expansion after being released from the delivery system (i.e., catheter) with the parachute element (and specifically the parachute element cover) serving to anchor and seal the first branch stent in position.

Figure 9J:
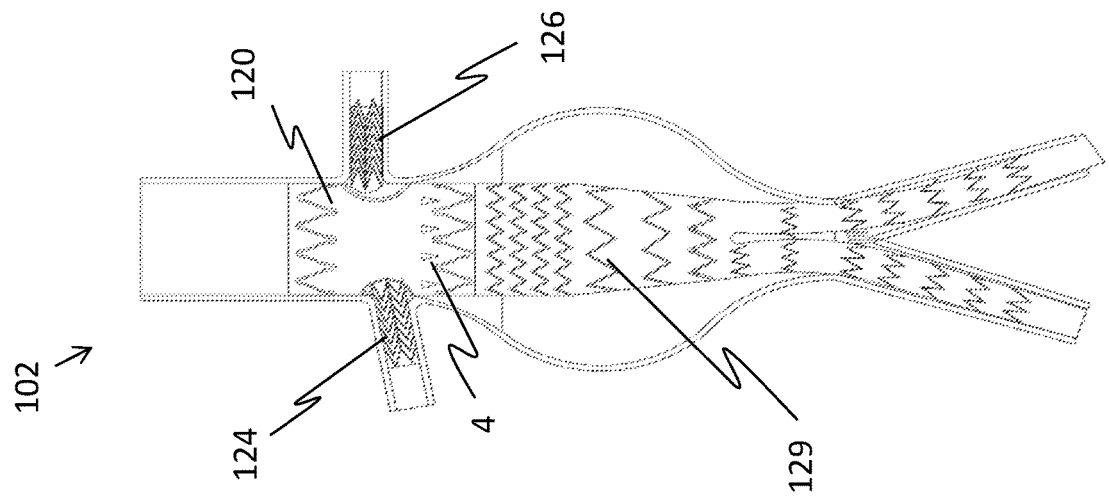
Figure 9I:
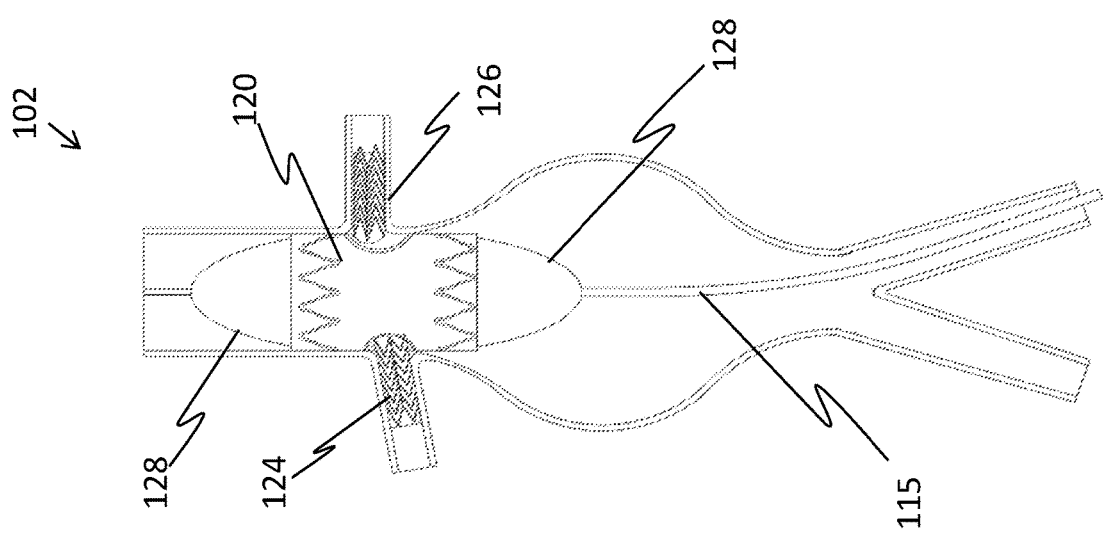
Figure 9H:
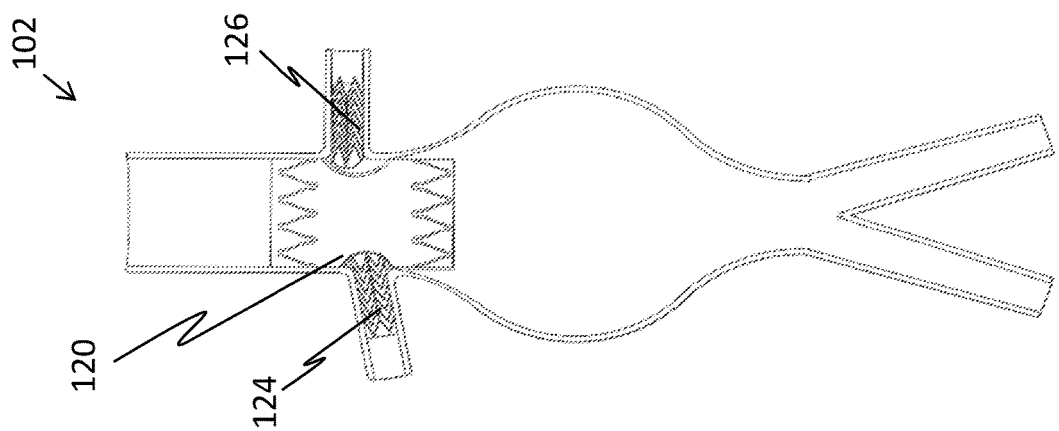

FIG. 9H shows a second branch stent 126, following deployment, in a similar fashion to that shown in FIGS. 9E through 9G hereinabove for first branch stent 124.

Referring to FIG. 9I, for robust fixation of the stent-graft to the aorta and better adaptation between the branch components and stent-graft, a balloon 128 is used to perform balloon dilatation. As opposed to prior art solutions that include balloon dilatation only at the distal end of the stent-graft (to enhance barb penetration of the aorta) embodiments of the current invention include balloon dilation of stent-graft along its entire length, including in the suprarenal zone and including branch components, for better stent-graft fixation and additionally to prevent endoleaks. "Full balloon dilation"—as described hereinabove—cannot typically be performed in conventional stent grafts, as noted above. Full balloon dilation is enabled in embodiments of the current invention due to integration of the parachute elements in the side stents—as noted hereinabove regarding FIG. 9G—which serve to retain and seal side stents in position with regard to the stent-graft, as described previously.

FIG. 9J shows a final configuration, after dilation of the stent graft and retraction of the catheter, after implantation of a typical endovascular Abdominal Aortic Aneurism (AAA) stent-graft into the suprarenal zone. Fenestrated stent graft 120 described hereinabove, which is a suprarenal aortic implant, serves as a robust end-anchoring platform for all types of currently-known AAA stent-grafts 129. Additionally shown in FIG. 9J are anchoring barbs 4 (as shown in FIG. 1A) which are deployed/used to anchor stent graft 129 to the fenestrated stent graft 120.

Reference is currently made to FIGS. 10A and 10B, which are sectional detailed views of Juxtarenal AAA configuration 102, as shown in FIGS. 9C and 9D, in accordance with embodiments of the current invention. Apart from the differences described below, Juxtarenal AAA configuration 102, its associated morphology, including primary blood vessel 103, and fenestrated stent graft 120 are identical in notation, configuration, and functionality to that shown in FIGS. 9C-9D, inter alia, and elements indicated by the same reference numerals and/or letters are generally identical in configuration, operation, and functionality as described hereinabove. As noted previously the uni-frame skeleton of the stent-graft may have extensions, which are connected to the delivery system by proximal and distal connections, 121 and 122, respectively. Additionally, an exemplary oversized fenestration 134, having a diameter of d1, is shown in alignment with second secondary blood vessel 106, having an internal diameter of d2. As described hereinabove, d1 is larger than d2. While not shown in the current figures, it is to be understood that embodiments of the current invention include other stent-graft oversized fenestrations being aligned with other secondary blood vessels, with respective diameters of the oversized fenestrations being larger than internal diameters of the secondary blood vessels, mutatis mutandis.

Reference is currently made to FIGS. 11A and 11B, which are representations of two alignment configurations of exemplary oversized fenestration 134 with second secondary blood vessel 106, as viewed from within the fenestrated stent-graft, implanted within primary blood vessel 102 of FIGS. 10A and 10B, with the branch stent of FIGS. 2A, inter alia, deployed and with the parachute element and parachute element cover 22 thereof likewise deployed, in accordance with embodiments of the current invention. Apart from the differences described below, parachute element cover 22, primary blood vessel 103, second secondary blood vessel 106, and oversized fenestration 134 are identical in notation, configuration, and functionality to that shown in FIGS. 2A and in FIGS. 10A and 10B, and elements indicated by the same reference numerals and/or letters are generally identical in configuration, operation, and functionality as described hereinabove.

Second secondary blood vessel 106 has a diameter of d1 and oversized fenestration 134 has a diameter indicated d2, with d1<d2.

FIG. 11A shows an ideal alignment configuration of the oversized fenestration with the second secondary blood vessel, whereas FIG. 11B shows a less-than-ideal alignment configuration. In both configurations, the branch stent is deployed in position, with the parachute element cover effectively serving as a seal to prevent endoleaks between the branch stent and the fenestration and as a branch stent-retention element, as described hereinabove.

Implantation and landing of the fenestrated stent-graft in the primary blood vessel is performed only when there is sufficient alignment between the oversized fenestration(s) and the secondary blood vessel(s). The options of recapturing and repositioning the stent-graft, and even fully retrieving the fenestrated stent-graft are available to either improve fenestration-side vessel alignment or to terminate the procedure—as previously noted.

Typically, patient selection and limitation checking criteria are known/determined before the procedure, based on patient vessel morphology, to enhance the chance of successful stent graft fenestrations alignment with branch vessel openings for single and multi-case branch vessel scenarios. Stent-graft implantation is of course contraindicated/not advised when patient morphology does not match the instruction for use criteria. Embodiments of the presented invention may be applied for aneurysms and aortic dissections, ascending and aortic arch zones and iliac aneurysms, and are not limited solely to endovascular treatment of complex AAA aneurysms. Treatment of other aneurysms may be performed using the same methodology as described and shown in FIGS. 9A-9J.

Reference is currently made to FIGS. 12A and 12B, which are schematic representations of aneurysms of an exemplary multi-branch artery 150, in which fenestrated stent-graft 120 and associated branch stents (for example, first branch stent 124, inter alia) are implanted, in accordance with embodiments of the current invention. Apart from the differences described below, fenestrated stent-graft 120 is identical in notation, configuration, and functionality to that shown in FIGS. 9H-9J and elements indicated by the same reference numerals and/or letters are generally identical in configuration, operation, and functionality as described hereinabove.

In FIG. 12A, the fenestrated stent-graft is a thoracic stent-graft, and the primary blood vessel is an ascending aorta that includes the aortic arch, as known in the art.

Another example of an aneurysm having a so-called zone 2-3 aortic arch is presented in FIG. 12B. In FIG. 12B, a branch component is implanted into the first secondary blood vessel (such as, but not limited to a brachiocephalic artery). As described in the methodologies presented in FIGS. 9A-9J and in FIGS. 11A-11B, a multi-branch implantation strategy may be implemented for three branch vessels of an aortic arch: brachiocephalic, left common carotid, and left subclavian arteries. The use of the branch components and dedicated fenestrations is applicable for a single-branch or multi branch configuration (i.e., a configuration having two or three secondary branch vessels).

As an alternative for Chimney techniques, the branch-stent (also referred to as "branch component") may be used as a stand-alone product without a dedicated fenestrated aortic stent-graft platform for an abdominal aortic aneurysm having a short neck smaller than 15 millimeters.

Respective stent-graft systems are defined by criteria for instructions for use. One of the criteria limiting the use of a specific stent-graft system is the length of the aortic neck. The nonadherence of instructions for use criteria of the stent-graft in endovascular repair is high, ranging from 38% to 68.9%. Nonadherence to proximal aortic neck instruction for use on its own has a strong correlation with negative outcomes, including increased endoleak, reintervention, and late death, as reported in Christine R. Herman at el., "Any nonadherence to instructions for use predicts graft-related adverse events in patients undergoing elective endovascular aneurysm repair", J. of VASC. SURG., January 2018.

Implantation of the stent-graft outside of the instruction for use criteria contributes to an increase in the relative risk of development of Type I endoleaks 4.5 times more in short-neck anatomy patients than in suitable-length neck anatomy patients, as measured during a 1-year follow-up. Aneurysms-related mortality risk is 9 times greater in the 1-year follow up, than in the short neck anatomy patients relative to suitable neck anatomy patients—as reported in G. A. Antoniou at el., "A meta-analysis of outcomes of endo-vascular abdominal aortic aneurysm repair in patients with hostile and friendly neck anatomy", J. of VASC. SURG., February 2013.

As noted previously hereinabove, to reduce endoleaks and aneurysm-related mortality, embodiments of the current invention are directed to use the side branch component as a stand-alone product with traditional off-the-shelf AAA stent-grafts, where the side branch component is implanted before implantation of the AAA stent-graft.

Prior art products, such as Cordis INCRAFT and Endologix OVATION AAA Stent Graft systems, may be suitable suit for implantation with embodiments of the current invention including the branch component. Such a technique promises superior results in the case of different heights between renal arteries and can also serve as an alternative for the single-branch Chimney technique for the lower artery and the implantation of the AAA outside of the instruction for use criteria. In cases of a multi-branch implantation, embodiments of the current invention are likewise applicable, using a fenestrated suprarenal aortic stent graft platform.

Reference is currently made to FIGS. 13A and 13B, which are schematic representations of the complex AAA short-neck configuration of the typical aortic renal zone configuration, as initially shown in FIGS. 1C-1E, inter alia, in accordance with embodiments of the current invention—including the branch stent discussed hereinabove in FIGS. 2A-2C, 3A-3C, 4A-4C, 5A-5C, 6A-6D, and 7A-7C, inter alia. Apart from the differences described below, fenestrated stent-graft 120, first branch stent 124, and currently-known AAA stent-grafts 129 are identical in notation, configuration, and functionality to that shown in previous figures and elements indicated by the same reference numerals and/or letters are generally identical in configuration, operation, and functionality as described hereinabove. Specifically, FIGS. 13A and 13B show a procedure where implantation of first branch stent 124 (also referred to as "branch component") is performed before implantation of the AAA stent graft, in the case of a short neck.

A typical endovascular implant, such as the stent-graft configurations presented in the current patent application, is intended to provide a conduit to exclude/redirect blood flow from an aneurysm. As compared to open surgical repair, patients treated with endovascular require more intensive follow-up, including annual imaging for the rest of their lives. After endovascular repair, patients are more likely to need additional interventions associated with their AAA.

The reasons for re-intervention include: losses of fixation or patency; aneurysm sac expansion; and inadequate exclusion of an aneurysm from blood flow and pressure, that is, an endoleak. Endoleaks are categorized by the source of the blood flow into the aneurysm sac. Lack of a seal at the proximal end of an endovascular graft or at the distal end of the endovascular graft are defined respectively as Type Ia and Type Ib endoleaks. Type Ib endoleaks occurs in a very rare cases and are caused by disengagement and relative migration of the iliac limb prosthesis, the legs of the aortic bifurcate prosthesis.

The branch stent configuration shown in FIG. 13A is also referred to as "a branch renal stent" hereinbelow. The branch renal stent, following implantation in the branch vessel, exhibits superior hemodynamic performance when compared with that of prior art (ie "conventional") renal stents for treatment of Renal Aortic Stenosis (RAS) and FEVAR, having a typical renal stent extention of 3 to 5 mm.

Prelimanry computational fluid dynamic (CFD) simulations serve to compare the blood flow reduction rate of an implanted prior art (i.e."conventional") branch renal stent, of approximately 30% of unimpeded branch blood flow with the blood flow reduction rate of the implanted branch renal stent of embodiments of the current invention, of approximately 18%. In other words, the branch renal stent of embodiments of the current invention has a substantially lower blood flowrate reduction of approximately 60% when compared with that of conventional branch renal stents (18%/30%=60%). Additionally, conventional renal stent extensions interfere with an aortic blood flow velocity profile, serving to reduce blood flow to an opposite renal artery, which may be critical for the patients having smaller aortic diameters, such as women and those of Asian origins.

As such, the branch renal stent serves as a superior solution for treatment of RAS and as an effective and unique endovascular solution for hypertension treatment based on Renin-Angiotensin-Aldosterone System (RAAS) for the patients having resistant hypertension (RHTN), as described further hereinbelow. Additionally, renal stenting in RAS patients with hypertension resistant to pharma treatment show clinically-approved evidence of blood pressure decrease, preserved renal function in a substantial proportion of patients, and improved LV structure and function in the long-term. Refer to Cristiana Catena et al. in "Long-Term Renal and Cardiac Outcomes after Stenting in Patients with Resistant Hypertension and Atherosclerotic Renal Artery Stenosis," Kidney Blood Press Res 2017;42:774-783, whose disclosure in incorporated by reference.

Renal artery stenosis compromises blood flow to the kidneys, which activates the renin-angiotensin-aldosterone axis and can lead to hypertension. In more than 90% of cases, renal artery stenosis is due to atherosclerosis, usually affecting the ostial part of the renal artery, as reported by Chrysochou C, Kalra PA, "Epidemiology and natural history of athero-sclerotic renovascular disease", Prog Cardiovasc Dis 2009; 52(3):184-195. doi:10.1016/j.pcad.2009.09.001, whose disclosure in incorporated by reference. Clinicians are encouraged to suspect renal artery stenosis and to look for it in patients having resistant hypertension, as it has been noted to be present in up to 24% of these patients, as noted by Benjamin MM et al., "Prevalence of and risk factors of renal artery stenosis in patients with resistant hypertension", Am J Cardiol 2014; 113(4):687-690, whose disclosure in incorporated by reference.

Optimal medical therapy remains the preferred treatment of atherosclerotic renal artery stenosis. Major society guidelines emphasize optimal medical therapy with blockade of the renin-angiotensin-aldosterone axis to confer survival benefit in these patients—as reported by Rooke TW et al; "Management of patients with peripheral artery disease (compilation of 2005 and 2011 ACCF/AHA Guideline Recommendations)", J Am Coll Cardiol 2013; 61(14):1555-1570, whose disclosure in incorporated by reference.

However, clinicians and researchers have long hoped that procedural intervention could relieve renal artery stenosis, cure hypertension, and eliminate the burden of lifelong medical therapy. In a pioneering work by Grüntzig et al, "Treatment of renovascular hypertension with percutaneous transluminal dilatation of a renal-artery stenosis". Lancet 1978; 1(8068):801-802, whose disclosure in incorporated by reference, using balloon angioplasty of renal artery stenosis, showed significant relief of hypertension. The subsequent development of vascular stents led to percutaneous revascularization by stenting as the preferred technique to resolve renal artery stenosis—as reported by Dorros G, Jaff M, Mathiak L, He T; Multicenter Registry Participants. "Multicenter Palmaz stent renal artery stenosis revascularization registry report: four-year follow-up of 1,058 successful patients", Catheter Cardiovasc Interv 2002; 55(2):182-188., whose disclosure is incorporated by reference.

There appears to be a broad expert consensus that certain groups of patients with severe renal artery stenosis should be treated with revascularization. Current American College of Cardiology/American Heart Association guidelines on the management of peripheral arterial disease give the procedure a Class IIa recommendation (level of evidence B) stating that percutaneous revascularization "is reasonable" for patients with hemodynamically significant renal artery stenosis and resistant hypertension. (Refer to Bailey SR et al. ACC/AHA/SCAI/SIR/SVM 2018 appropriate use criteria for peripheral artery intervention: a report of the American College of Cardiology Appropriate Use Criteria Task Force, American Heart Association, Society for Cardiovascular Angiography and Interventions, Society of Interventional Radiology, and Society for Vascular Medicine. J Am Coll Cardiol 2019; 73(2):214-23, whose disclosure is incorporated by reference.

Similarly, a statement by the Society for Cardiovascular Angiography and Interventions suggests percutaneous revascularization may be considered as appropriate care in patients with significant renal artery stenosis and resistant hypertension, as reported by Parikh SA, at el., "SCAI expert consensus statement for renal artery stenting appropriate use", Catheter Cardiovasc Interv 2014; 84(7):1163-1171, whose disclosure is incorporated by reference.

In one of the largest randomized controlled trials to date, the Cardiovascular Outcomes in Renal Atherosclerotic Lesions (CORAL study), with 947 patients in total, the rates of end points were similar between the percutaneous revascularization group and the medical therapy-only group at 43 months of follow-up, as noted by Cooper CJ, Murphy TP, Cutlip DE, et al; CORAL Investigators. Stenting and medical therapy for atherosclerotic renal-artery stenosis. N Engl J Med 2014; 370(1):13-22, whose disclosure is incorporated by reference.

In an additional study, reported by Wheatley K, Ives N, Gray R, et al (ASTRAL Investigators), in the Angioplasty and Stenting for Renal Artery Lesions (ASTRAL) trial, "Revascularization versus medical therapy for renal-artery stenosis", N Engl J Med 2009; 361(20):1953-1962, whose disclosure is incorporated by reference, over the same time, the mean serum creatinine level was 1.6 µmol/L lower in the revascularization group than in the medical therapy group.

Thus, percutaneous revascularization for renal artery stenosis appears to have a reasonable renal safety profile—even in patients with chronic kidney disease (CKD). This infers that the hemodynamically and morphologically optimized solution, as described by embodiments of the current invention, that clinical results should be superior that those after prior art renal stenting or FEVAR.

Reference is currently made to FIGS. 14A and 14B, which are schematic representations of a typical aortic renal zone configuration 200 showing prior art Type Ia endoleaks 205. Type Ia endoleaks occur much more often than Type Ib leaks and are riskier, because pressure remains on the aortic wall and there is frequently an unimpeded antegrade flow into the aneurysm sac. Due to continued pressurization of the aortic sac, Type Ia endoleaks may lead to a late rupture of aneurysms and therefore require intervention whenever they are encountered.

The typical EVAR implant usually uses two configurations of anchoring to the blood vessel for AAA repair. One configuration uses a bare metal proximal aortic stent with open or closed-cell design, with proximal fixation barbs (FIG. 14A). A proximal aortic stent, usually fabricated with an additional cone flare and having a more robust strut design than other rings in the implant, provides greater radial force on the vessel in the landing zone area. Typically, implantation of a proximal aortic stent occurs in the aortic suprarenal zone and renal arteries and serves as a marker during the EVAR procedure.

Another configuration is the location of fixation barbs 4 on the implant proximal line of the EVAR implant (FIG. 14B). In this configuration, the EVAR implant is deployed below the first secondary blood vessel 104 (in this case, corresponding to the lower renal artery). In both endo-anchoring configurations, in some patients, Type Ia endoleak occurs during long-term clinical follow-up study.

Embodiments of the current invention including the suprarenal multi-stent configuration having chronology steps shown in FIGS. 9A-9I can be directed to be deployed in the aortic suprarenal zone for both endo-anchoring EVAR configurations noted hereinabove and can serve to prevent endoleak Type Ia (FIG. 14B).

Reference is currently made to FIG. 15, which is a schematic representation of the complex AAA typical aortic renal zone configuration, as initially shown in FIGS. 1C-1E and FIGS. 13A-13B, inter alia, with the EVAR implant first implanted into the primary blood vessel and with the suprarenal multi-stent configuration subsequently implanted, in accordance with embodiments of the current invention.

The terms "multi-stent" and "multi-stent configuration" are intended to mean fenestrated stent graft 120 and side stents (such as, but not limited to first branch stent 124), together. Apart from the differences described below, fenestrated stent-graft 120, first branch stent 124, and prior art AAA stent-grafts 129 are identical in notation, configuration, and functionality to that shown in previous figures and elements indicated by the same reference numerals and/or letters are generally identical in configuration, operation, and functionality as described hereinabove.

Fixation barbs 4 were applied when AAA stent-graft 129 was initially implanted. Currently, a proximal sleeve 220 of the fenestrated stent-graft (most of which is not visible in the current figure) is inserted within AAA stent-graft 129. In this way, endoleaks described and shown in FIGS. 14A and 14B hereinabove are obviated.

Embodiments of the current invention, including the EVAR procedure disclosed herein, are limited by the outer diameter of the AAA stent graft catheter, and typical FEVAR solutions are limited to a 6.7 to 8.0 mm outer diameter size, which may support only 50% of male and 15% of female patients. Additionally, women with AAA have a shorter time window for treatment as their AAA expands faster and ruptures at smaller diameters—as reported by Lo et al., "Gender differences in abdominal aortic aneurysm presentation, repair, and mortality in the Vascular Study Group of New England", Journal of Vascular Surgery, Vol. 57, issue 5, pp. 1261-1268, May 2013.

Embodiments of the present invention may also be used as a suprarenal sealing implant for EVAR secondary intervention. In addition to the Juxtarenal Abdominal Aortic Aneurysm (AAA); Pararenal AAA; and Suprarenal AAA—as described hereinabove—embodiments of the present invention may also be applied to aneurysms, including, but not limited to: an Aortic Root Aneurysm; an Aortic Arch Aneurysm; a Thoracoabdominal Aortic Aneurysm; an Iliac Artery Aneurysm; and an Internal Iliac Artery Aneurysm.

It will be appreciated that the above descriptions are intended only to serve as examples and that many other embodiments are possible within the scope of the present invention as defined in the appended claims.

The invention claimed is:

1. A multi-stent system comprising a plurality of branch stents and an oversized-fenestrated stent-graft, the multi-stent system is configured to use a delivery system to deliver to an intervascular bifurcation zone, the bifurcation zone having a main blood vessel and a plurality of side blood vessels having respective side blood vessel diameters, the side blood vessels branching out of the main blood vessel, and each of the plurality of branch stents comprising:
    a tubular element having an unconstrained shape, including: an axis of elongation; a first tubular element end; a second tubular element end; and a tubular element cover, the tubular element extending between first and second tubular element ends; and
    a parachute element having an unconstrained shape, including a substantially curved-toroidal/disc configuration and a loop reinforcement element, the parachute element having a parachute element cover, the parachute element positioned substantially at the second tubular element end and the parachute element positioned perpendicularly and coaxially to the axis of elongation;
    wherein each of the plurality of branch stents is configured to be implanted from within the oversized-fenestrated stent-graft having oversized fenestrations, the oversized-fenestrated stent-graft configured to be first implanted in the main blood vessel at the bifurcation zone, with each of the oversized fenestrations having respective diameters larger than respective side blood vessel diameters;
    wherein the oversized-fenestrated stent-graft has a uni-frame skeleton having a series of closed cells pattern, the oversized-fenestrated stent-graft having a proximal and a distal extension, the proximal and distal extensions not covered with any fabric or polymer;
    wherein the proximal and distal extensions are configured to be connected to the delivery system by a proximal connection and a distal connection, and wherein the oversized-fenestrated stent-graft is configured for full control of radial expansion during deployment, including recapturing, repositioning, and fully retrieving the fenestrated stent-graft back into the delivery system and removal from the body if necessary;
    wherein the oversized-fenestrated stent graft is further configured to be deployed without target catheters occupying the plurality of side blood vessels; and the oversized-fenestrated stent graft is additionally configured to not interfere with blood flow through the main blood vessel and the plurality of side blood vessels during deployment; and
    wherein each of the parachute element covers is configured to prevent endoleaks from a main blood vessel blood flow to an aneurysm sac following deployment of the multi-stent system.

2. The multi-stent system of claim 1, wherein the oversized fenestrations are non-customized and are not based on a specific morphology.

3. The multi-stent system of claim 2, wherein the delivery and deployment of the multi stent are part of an endovascular aneurysm repair (EVAR) procedure and wherein the bifurcation zone includes at least one aneurysm chosen from the group including: a Juxtarenal Abdominal Aortic Aneurysm (AAA); a Pararenal AAA; a Suprarenal AAA; an Aortic Root Aneurysm; an Aortic Arch Aneurysm; and a Thoracoabdominal Aortic Aneurysm.

4. The multi-stent system of claim 3, wherein the delivery and deployment of the multi-stent system are sub-procedures of the EVAR procedure, the sub-procedures including a singular insertion and associated withdrawal of the delivery system or components thereof, directed to reduce a chronology of the procedure.

* * * * *